(12) United States Patent
Wallsten

(10) Patent No.: US 9,283,108 B2
(45) Date of Patent: Mar. 15, 2016

(54) STERILISATION DEVICE

(76) Inventor: Hans I. Wallsten, Paudex (CH)

(*) Notice: Subject to any disclaimer, the term of this patent is extended or adjusted under 35 U.S.C. 154(b) by 457 days.

(21) Appl. No.: 13/502,699

(22) PCT Filed: Dec. 14, 2010

(86) PCT No.: PCT/EP2010/069668
§ 371 (c)(1),
(2), (4) Date: Apr. 18, 2012

(87) PCT Pub. No.: WO2011/064408
PCT Pub. Date: Jun. 3, 2011

(65) Prior Publication Data
US 2012/0209295 A1    Aug. 16, 2012

(30) Foreign Application Priority Data

Nov. 26, 2009  (EP) .................................... 09177213
Sep. 15, 2010  (EP) .................................... 10176935

(51) Int. Cl.
*A61B 18/04* (2006.01)
*A61M 31/00* (2006.01)
*A61F 6/22* (2006.01)
(Continued)

(52) U.S. Cl.
CPC ................. *A61F 6/225* (2013.01); *A61B 18/04* (2013.01); *A61B 2017/4233* (2013.01); *A61B 2018/0063* (2013.01); *A61B 2018/00559* (2013.01); *A61B 2018/044* (2013.01); *A61B 2018/046* (2013.01)

(58) Field of Classification Search
CPC ...... A61B 18/04; A61B 18/082; A61B 18/10; A61B 2018/00559; A61B 2018/00577; A61B 2018/00595; A61B 2018/0063; A61B 2018/044; A61B 2018/046; A61B 2018/048; A61B 17/42; A61B 17/425; A61B 2017/42; A61B 2017/4216; A61B 2017/4233; A61F 6/22; A61F 6/225; A61F 7/12; A61F 7/123
See application file for complete search history.

(56) References Cited

U.S. PATENT DOCUMENTS

| 3,822,702 A | 7/1974 | Bolduc et al. |
| 3,875,939 A | 4/1975 | Bolduc et al. |

(Continued)

FOREIGN PATENT DOCUMENTS

WO   WO-96/15740 A1   5/1996

OTHER PUBLICATIONS

International Search Report PCT Form PCT/ISA/210.
(Continued)

*Primary Examiner* — Jonathan W Miles
*Assistant Examiner* — Todd J Scherbel
(74) *Attorney, Agent, or Firm* — Harness, Dickey & Pierce, P.L.C.

(57) ABSTRACT

Apparatus for sterilization of a female mammal comprising at least one separation member for separation of a fallopian tube from a uterine cavity of the female mammal, a circulation assembly which is operatively connected to said at least one separation member, and at least one sterilization lumen which is operatively connected to said circulation assembly and debouching at a distal side of said at least one separation member, said at least one sterilization lumen being adapted for injection in use of a tissue necrotizing fluid capable of necrotizing a lining of at least a part of said fallopian tube, wherein said circulation assembly is adapted to circulate said tissue necrotizing fluid within said sterilization lumen and said fallopian tube. The apparatus allows quick, simple, safe and reliable sterilization.

46 Claims, 19 Drawing Sheets

(51) Int. Cl.
*A61B 17/42* (2006.01)
*A61B 18/00* (2006.01)

(56) References Cited

U.S. PATENT DOCUMENTS

| | | | |
|---|---|---|---|
| 3,924,628 A | | 12/1975 | Droegemueller et al. |
| 3,972,331 A | | 8/1976 | Bolduc et al. |
| 4,119,098 A | | 10/1978 | Bolduc et al. |
| 4,182,328 A | | 1/1980 | Bolduc et al. |
| 4,601,698 A | * | 7/1986 | Moulding, Jr. ............... 128/831 |
| 5,542,928 A | * | 8/1996 | Evans et al. ................. 604/113 |
| 5,549,559 A | | 8/1996 | Eshel |
| 5,653,692 A | * | 8/1997 | Masterson et al. ............ 604/113 |
| 5,704,934 A | | 1/1998 | Neuwirth et al. |
| 6,187,346 B1 | | 2/2001 | Neuwirth |
| 6,960,203 B2 | * | 11/2005 | Xiao et al. ..................... 606/27 |
| 2003/0208156 A1 | * | 11/2003 | Pham et al. ................... 604/113 |
| 2005/0192652 A1 | * | 9/2005 | Cioanta et al. ................ 607/105 |
| 2005/0240211 A1 | | 10/2005 | Sporri et al. |
| 2007/0088344 A1 | | 4/2007 | Schechter et al. |
| 2008/0154238 A1 | * | 6/2008 | McGuckin ..................... 604/515 |
| 2009/0082837 A1 | | 3/2009 | Gellman et al. |
| 2009/0125010 A1 | | 5/2009 | Sharkey et al. |
| 2010/0082021 A1 | | 4/2010 | Gutierrez et al. |
| 2012/0209295 A1 | * | 8/2012 | Wallsten ....................... 606/135 |

OTHER PUBLICATIONS

Swedish Novelty Search Report.

* cited by examiner

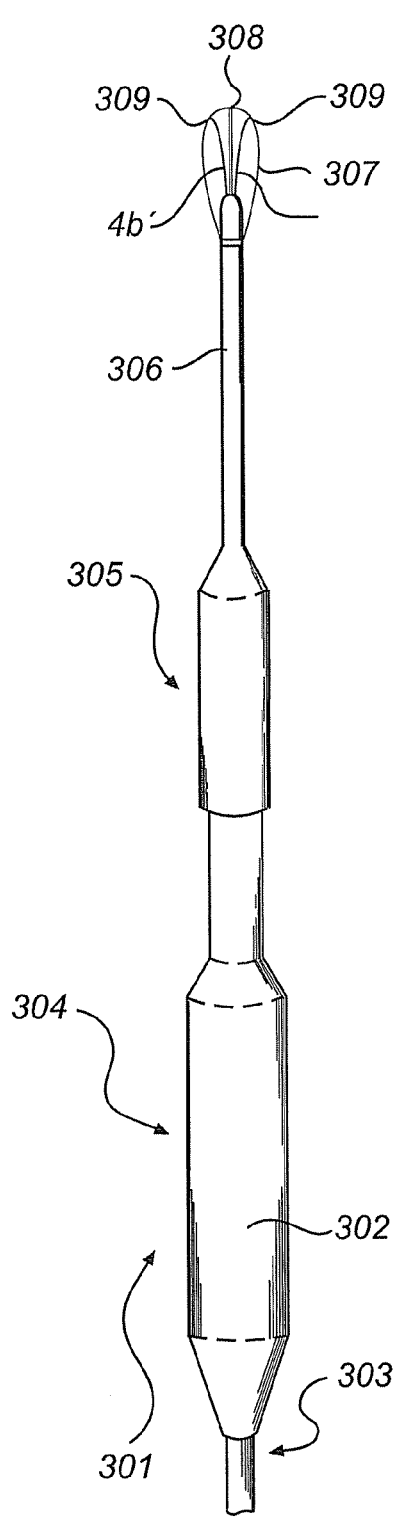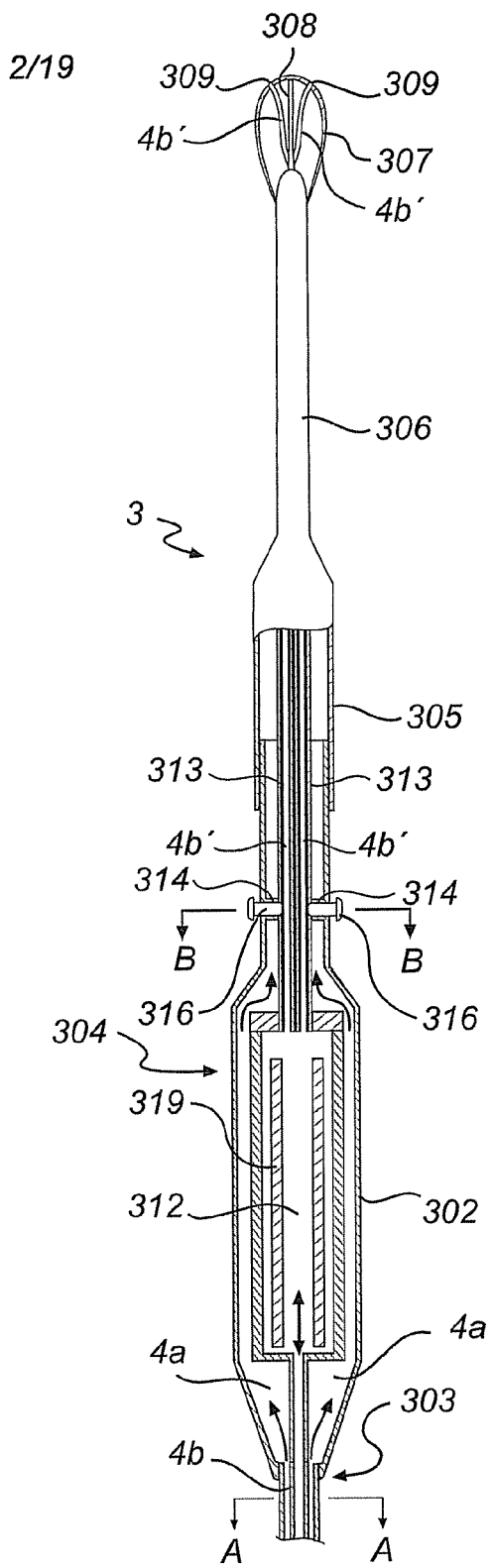
Fig. 1b
Fig. 1c

A-A

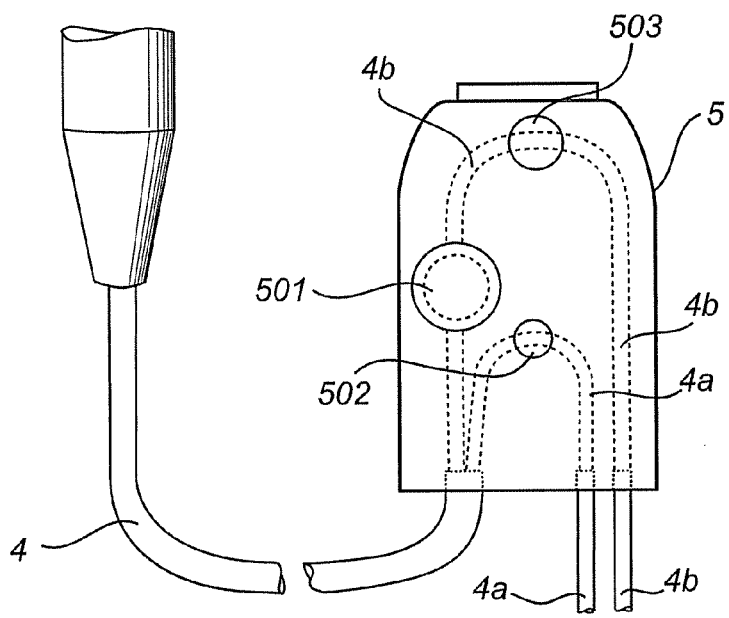
Fig. 1g
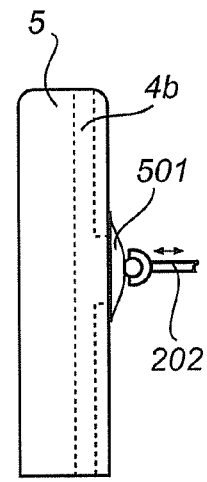
Fig. 1i
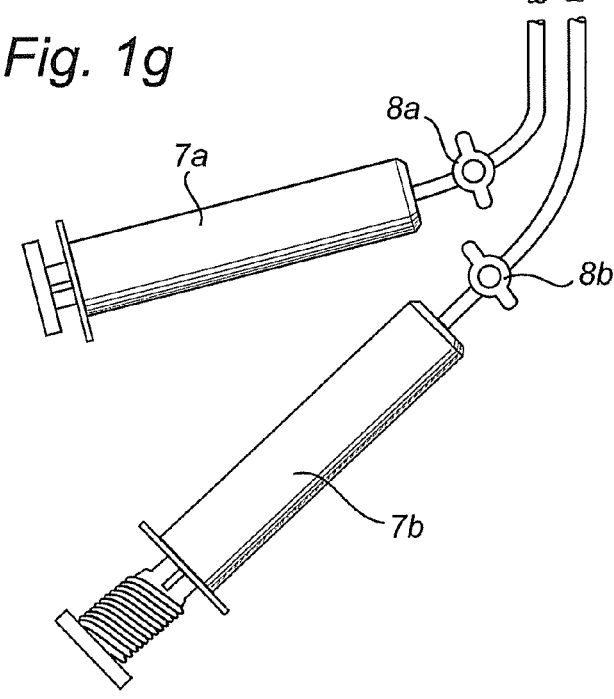
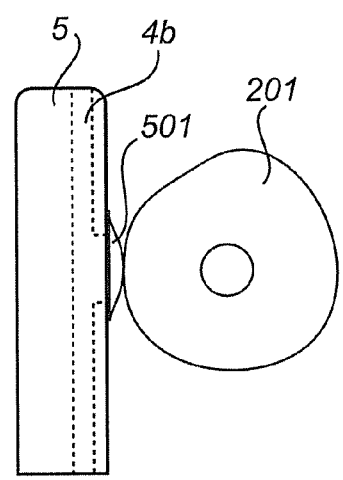
Fig. 1h

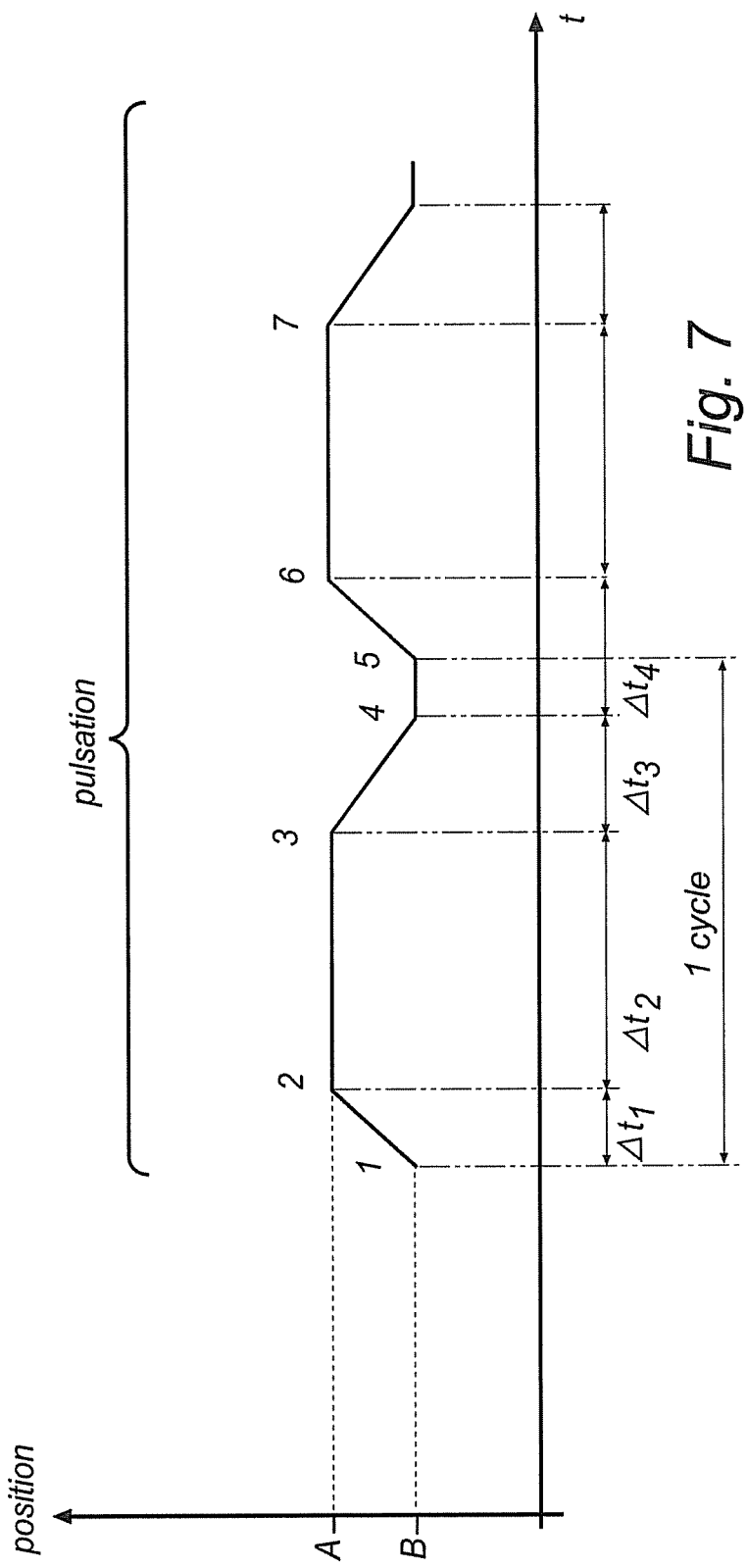

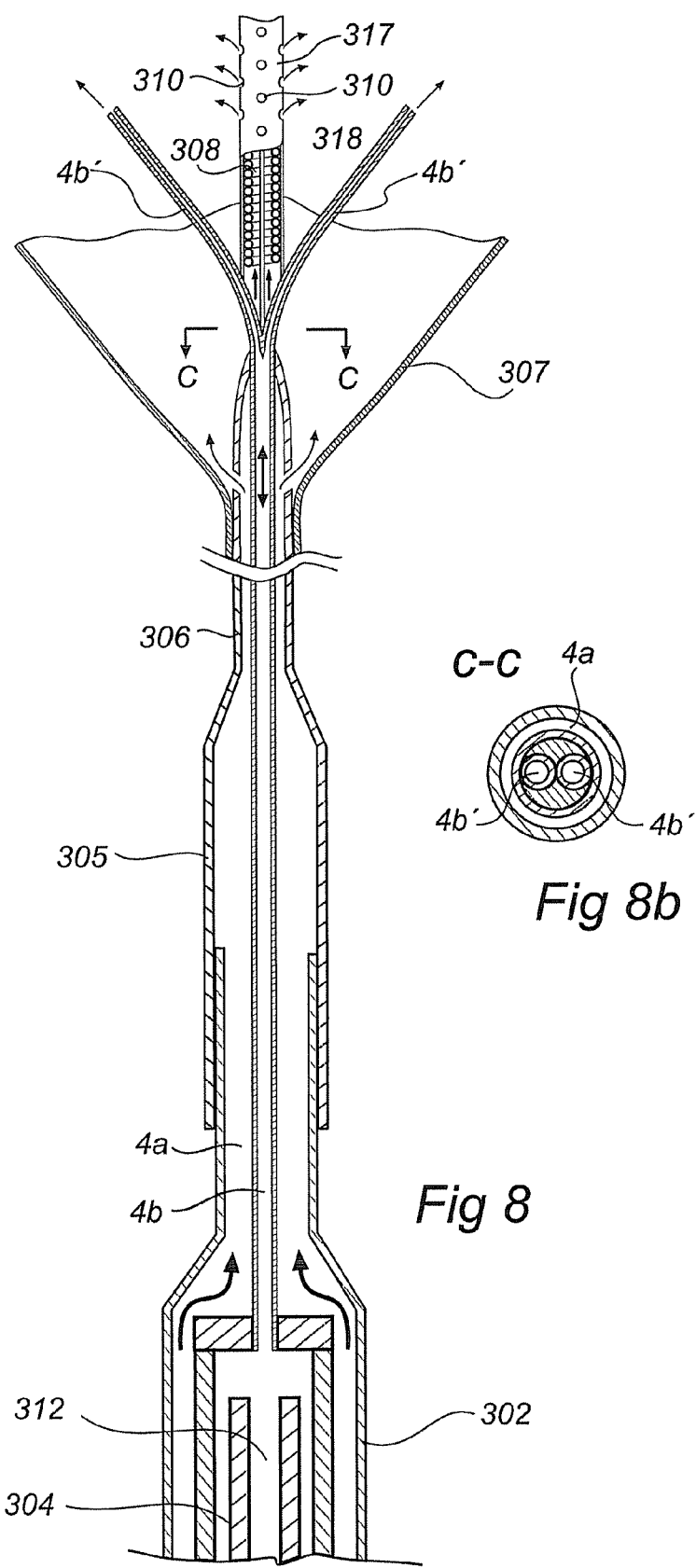

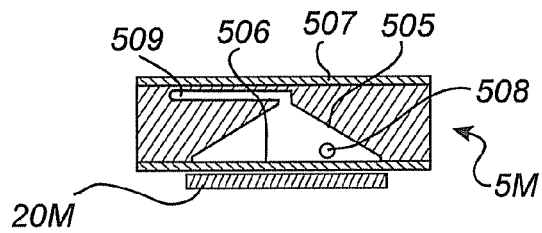
Fig. 10b
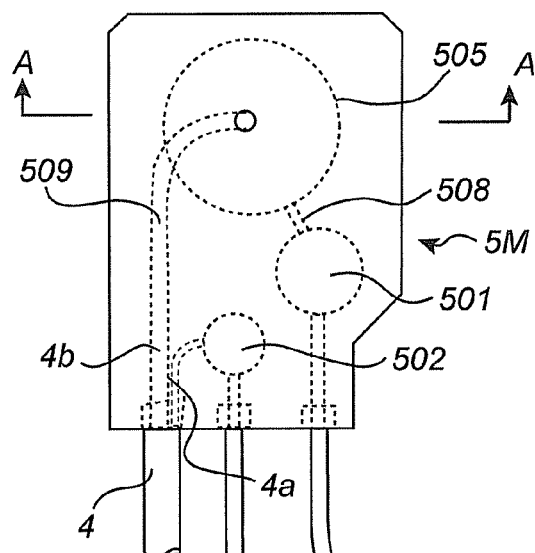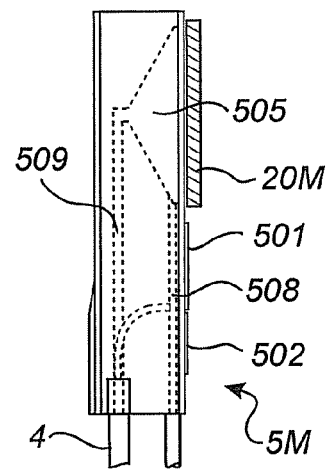
Fig. 10c
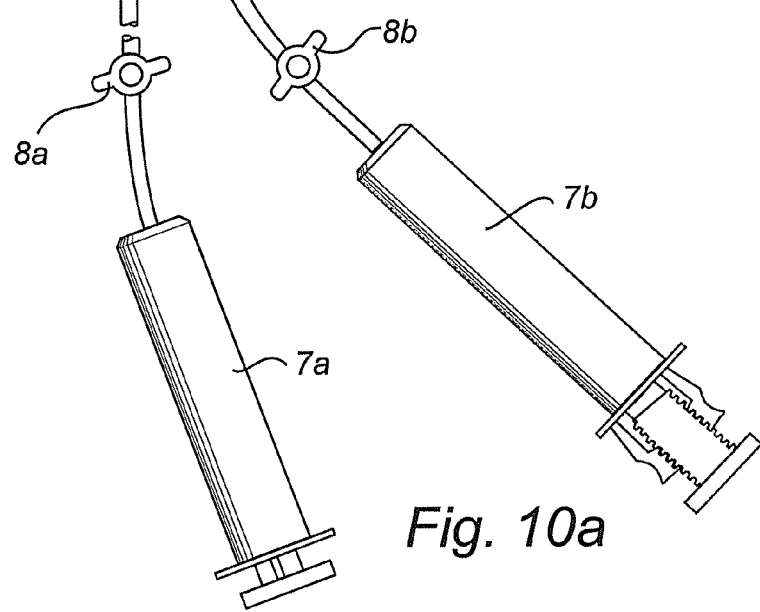
Fig. 10a

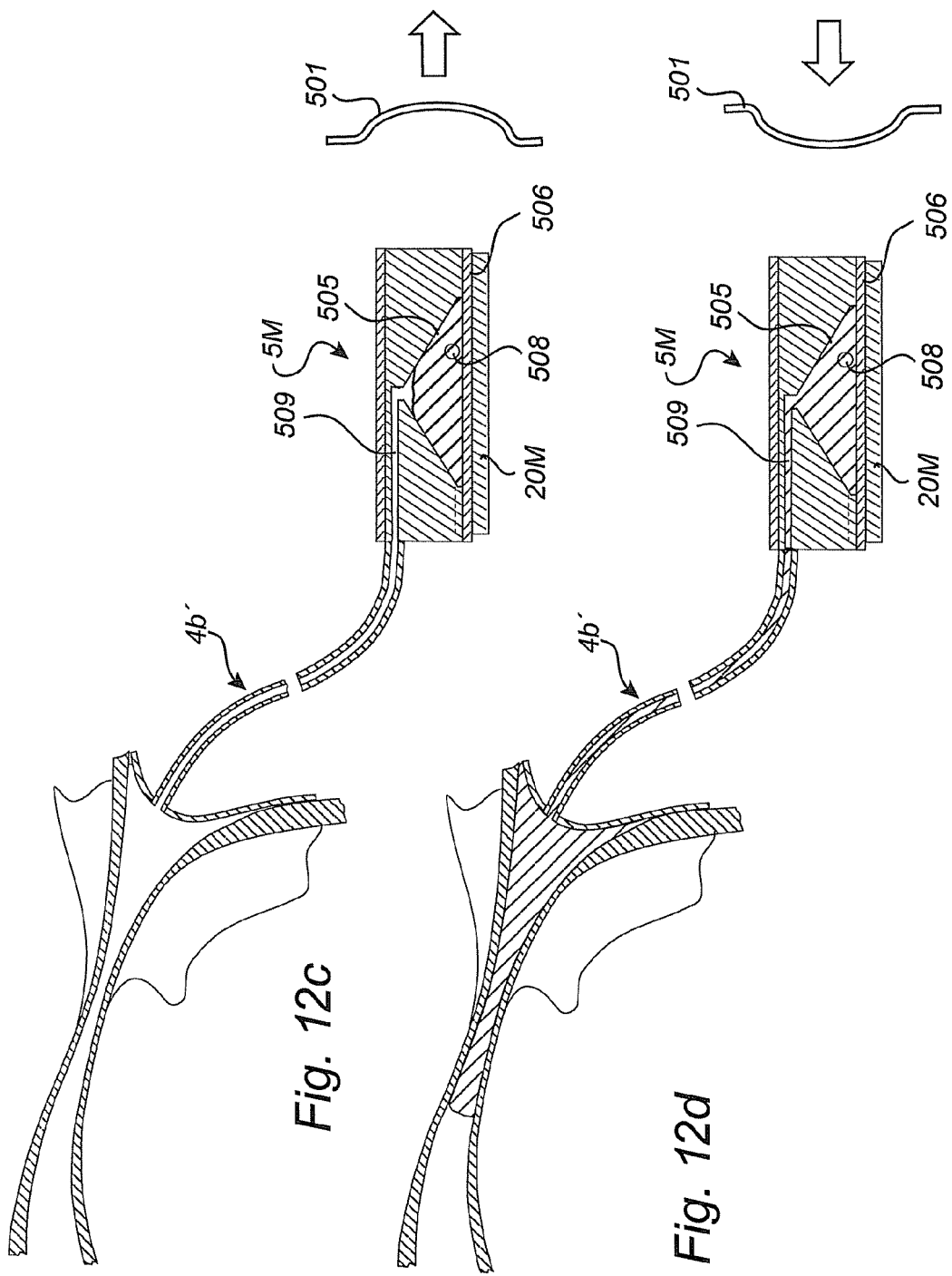

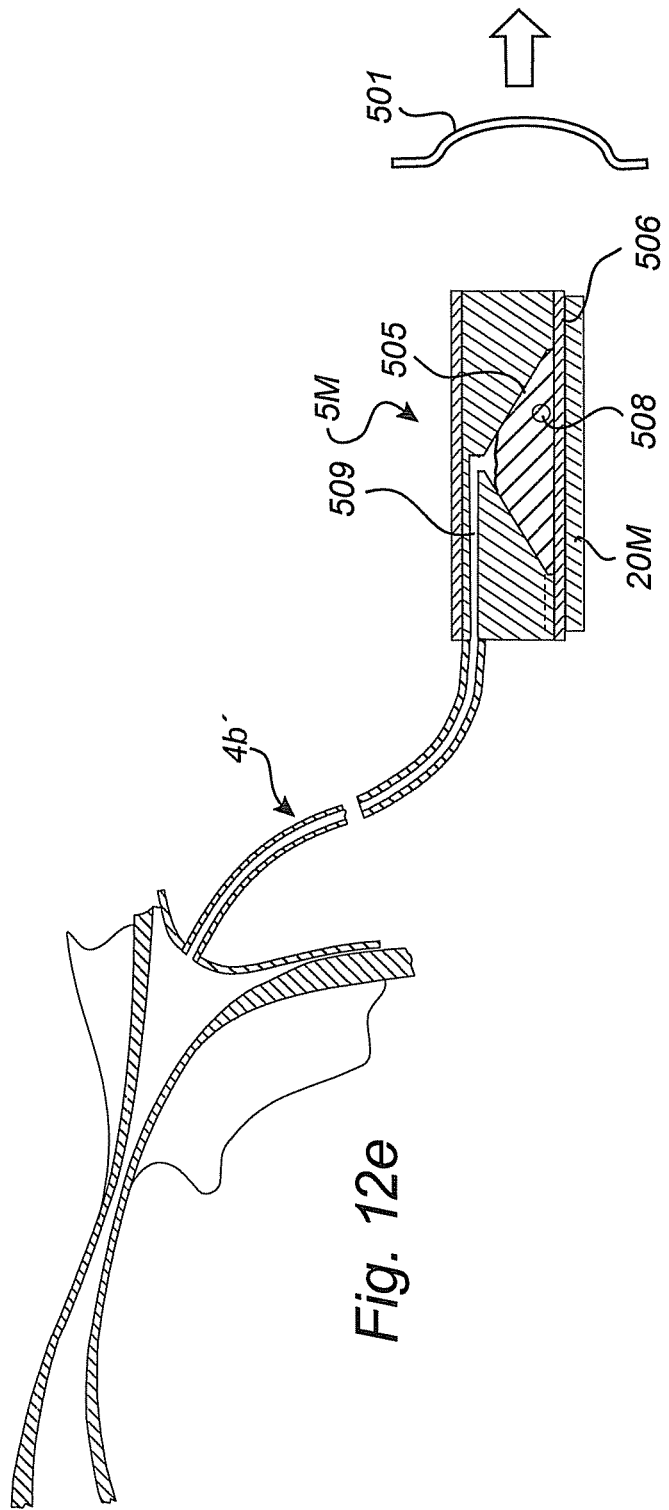

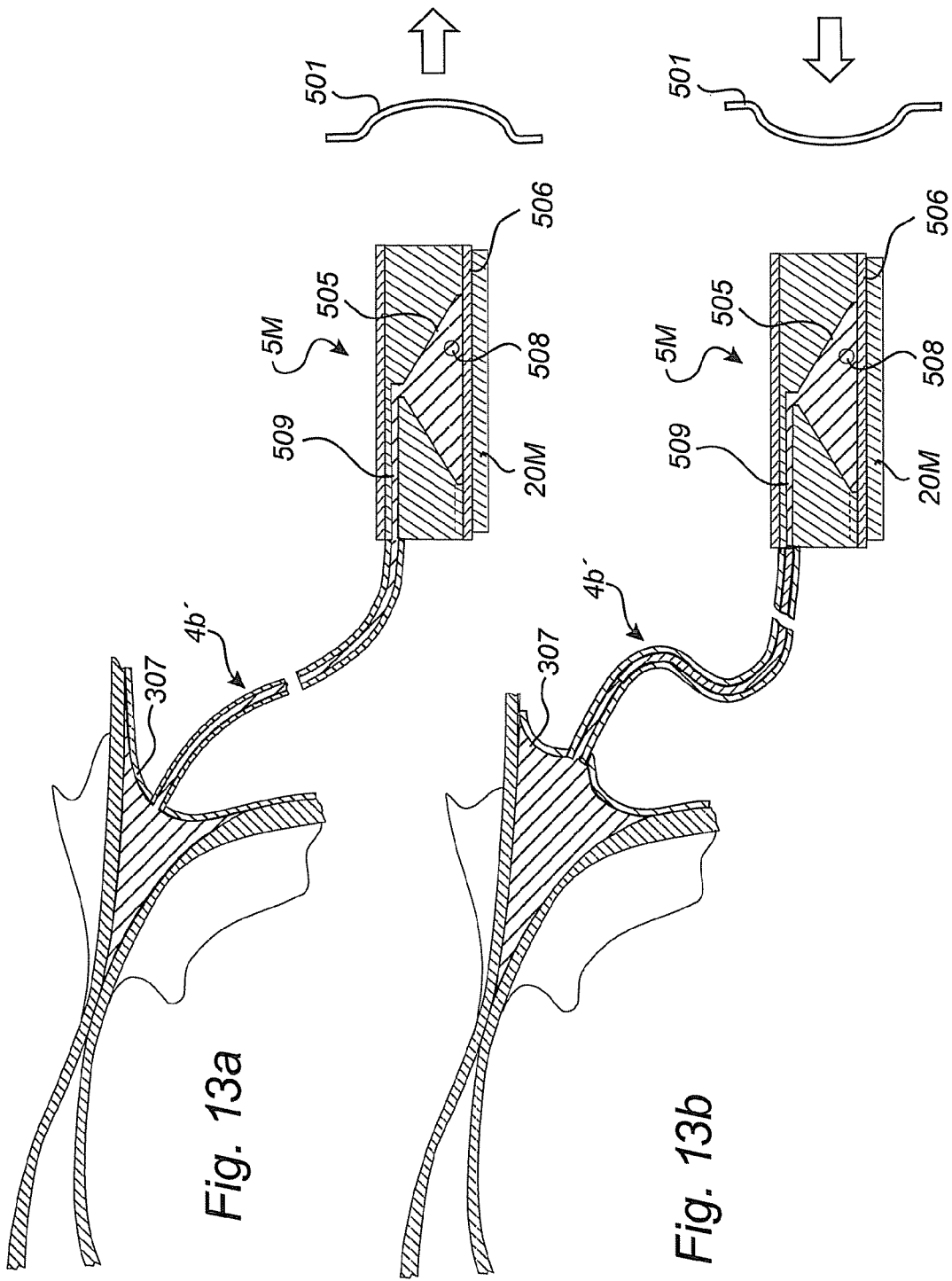

STERILISATION DEVICE

FIELD OF THE INVENTION

The present invention relates to an intracervical method for sterilisation of a female mammal and an apparatus for performing said method.

TECHNICAL BACKGROUND

Sterilisation of women may be made for many reasons. Generally it can also be said that there is a great need for sterilisation. There are also a number of different methods used. The most common method is to clamp or cut off the fallopian tubes by external surgery in order to hinder sperms from reaching the ovum. This is an external invasive method which as such is risky for the patient and requires hospital time. Several less invasive methods have been suggested to reduce the risks associated with surgical methods, and to reduce the costs for time and hospital care. Some less invasive methods are performed intracervically under direct visual observation by the use of a hysteroscope and a special catheter through which an agent can be introduced into the fallopian tube via the cornu of the uterus with the aim to block the fallopian tube. One such method is based on the use of a silicone plug sold under the name of OVABLOC. However, the method is difficult to perform, and there is also a risk that the silicone plug will fall out of the fallopian tube due to the powerful movements or spasms of the tube.

Other less invasive sterilisation methods include the administration of a toxic substance using a catheter introduced into the inlet of the fallopian tube. The toxic substance causes the tissue of the fallopian tube to necrotise and thus produces scar tissue which blocks the tube. However, such substances are not only toxic to the tissue of the fallopian tube, but also to the surrounding tissues. Since such toxic substances may enter into the abdominal cavity via the fallopian tube, there is a risk of serious damage. The manner in which to handle this problem is usually to thoroughly measure and monitor the volume of toxic substance introduced. Moreover, use of toxic substances as such should be limited to a minimum because of general safety and environmental concern. For the above reasons, this technique has not been used in the western world.

Furthermore, a method has also been proposed which involves the administration of hot sterile water by continuous infusion of the hot water through the fallopian tube, which can cause a part of the tissue of the fallopian tube to necrotise and thus produce scar tissue which, over some time, would block a part of the tube. The cooled water would then go down into the abdomen cavity. It is however vital that a temperature of at least 60-90° C., or even higher, is maintained in the part of the fallopian tube to be treated for a sufficient amount of time.

Medically, the fallopian tube comprises different sections as seen in its lengthwise direction and two sections suitable for treatment are the intramural section and the isthmus in particular. The intramural section, which is located close to the cornu, has the smallest diameter of about 1 mm and is approx. 10 mm long, and is highly vascularised. In the water infusion method described above, it is vital that a correct amount of hot sterile water is infused through the fallopian tube at a proper balance between infusion speed and water temperature. The blood circulation in the intramural section has a strong cooling effect and if the speed of the water is too low, the water may when reaching the isthmus section, already have been so cooled that no efficient sterilisation can occur. On the other hand, if the speed of the hot water is too high, hot water may pass through the fallopian tube to reach the abdominal cavity, with high risk for damage in the form of adhesions. Furthermore, large amounts of water in the abdominal cavity might be taken up by the vascular system, and subsequently cause major damage to the brain. The method seems not to have been used in practice.

There are also other methods suggested for the occlusion of the fallopian tubes by using catheters creating locally high temperature, based on radio frequency or electrically heated filaments. Such methods however require the use of a hysteroscope, which is a disadvantage. Furthermore, the catheters have to be introduced into the tubes to a sufficient length in order to assure 100% occlusion of the fallopian tube, with high risk for damage. In addition, such methods must be performed twice, i.e. once for each fallopian tube, thus increasing the risk for damage.

In this respect it is also vital to mention that the fallopian tube may obstruct such sterilisation methods. A tube may be fully or partially blocked, and although it may be fully blocked this needs to be confirmed. In some cases, a fallopian tube merely provides some resistance to the sterilisation instruments and/or substances and thus must to be opened, which is difficult to achieve. This step of confirmation of an open fallopian tube has to be performed initially as a separate step before the sterilisation method is performed.

It is therefore the object of the present invention to provide a sterilisation device, and sterilisation method using said device, that is non-invasive and which is simple to use, yet overcomes at least some of the disadvantages mentioned above. It should preferably also operable by someone other than a highly qualified gynaecologist and under conditions that would not necessitate a fully sterilised operating theatre.

SUMMARY OF THE INVENTION

These and other objects of the present invention are achieved by an apparatus and/or a method, respectively, as defined in the independent claims.

In a first aspect, the invention provides an apparatus for sterilisation of a female mammal comprising at least one separation member for separation of a fallopian tube from a uterine cavity of the female mammal, a circulation assembly which is operatively connected to said at least one separation member, and at least one sterilisation lumen which is operatively connected to said circulation assembly and debouching at a distal side of said at least one separation member. The at least one sterilisation lumen is adapted for injection in use of a tissue necrotising fluid capable of necrotising a lining of at least a part of said fallopian tube. The circulation assembly is adapted to circulate said tissue necrotising fluid within said sterilisation lumen and said fallopian tube.

The apparatus of the invention allows simple and safe sterilisation of the female mammal. It can be used by an operator which does not have advanced medical training, and it does not require the co-operation of extensive surgical or other medical equipment. Furthermore, by using a tissue necrotising fluid occlusion of the fallopian tube is achieved through the formation of scar tissue at the necrotised area, thus avoiding the use of a foreign object, such as a plug, which might be dislocated due to spasms of the fallopian tube. Thus, the apparatus allows permanent, reliable sterilisation.

Typically, the distal end of said sterilisation lumen may comprise at least one debouching opening and in use is positioned in or in the proximity of said fallopian tube. Furthermore, in embodiments of the invention, the apparatus may comprise two sterilisation lumens, each debouching in or in the proximity of a separate fallopian tube. The presence of two sterilisation lumens, one for each tubal ostium, enables simultaneous treatment of both fallopian tubes. However, the presence of two sterilisation lumens also facilitates consecutive treatment of the fallopian tubes, since a sterilisation lumen used for treatment of the first fallopian tube need not be repositioned for treatment of the second fallopian tube. Hence, in embodiments of the invention, the circulation assembly and the sterilisation lumens may be adapted for treatment of both fallopian tubes simultaneously. Simultaneous treatment of both fallopian tubes may reduce the total time needed for treating the female mammal.

The at least one separation member is typically adapted to separate the tubal ostium of a fallopian tube from the uterine cavity of the female mammal. Optionally, the separation member is adapted to simultaneously separate both fallopian tubes from the uterine cavity.

In embodiments of the invention the at least one separation member comprises an inflatable member. An inflatable separation member allows easy introduction into the uterine cavity via the cervix when deflated without necessitating the use of a hysteroscope. Also, an inflatable separation member may facilitate the positioning of the debouching opening of the sterilisation lumen in or in the proximity of the tubal ostium. In such embodiments, the sterilisation apparatus further comprises an inflation assembly adapted to inflate said inflatable member, typically by introducing an inflation fluid, via at least one inflation lumen.

The at least one sterilisation lumen may positioned within said inflatable member.

In embodiments of the invention, the circulation assembly may be adapted to heat said tissue necrotising fluid to a temperature of about 65-180° C., and preferably about 75-90° C. Such temperatures are suitable for achieving sufficient necrotisation of the tubal lining within a short period of time. The heating may be achieved by means of a heater provided on a proximal side of the at least one separation member and adapted to heat said tissue necrotising fluid. Thus, the heater need not be located in the part of the sterilisation apparatus which is to be inserted into the female mammal.

The circulation assembly may be adapted to circulate said tissue necrotising fluid by means of a first membrane, which is operatively connected to a driving mechanism and to said at least one sterilisation lumen, and arranged such that said tissue necrotising fluid is urged into circulation upon movement of the membrane. The circulation of fluid described herein may be of a fluid column oscillating between the sterilisation lumen and the fallopian tube. By the use of a membrane which on one side may be in contact with the tissue necrotizing fluid, the driving mechanism need not be in direct contact with the sterile tissue necrotizing fluid. Such a design allows the sterilisation lumen and the membrane to be made as sterile, disposable parts, while the driving mechanism may be non-sterile and reusable.

In embodiments where the apparatus comprises at least two sterilisation lumens, a clamping device may be provided which is operatively connected to the sterilisation lumens and arranged to separately clamp one of said two sterilisation lumens so as to prevent passage of fluid through said one sterilisation lumen. Thus, while the apparatus comprises two sterilisation lumens allowing simultaneous treatment of the fallopian tubes, an operator may choose to treat only one fallopian tube at a time by clamping the sterilisation lumen of the other fallopian tube. Furthermore, in such embodiments, the apparatus may also comprise a pressure sensor arranged to detect a fluid pressure in one of said two sterilisation lumens. Thus, the resistance of the fallopian tube to the injection of fluid may be monitored, facilitating the detection of a full or partial occlusion of the fallopian tube.

In embodiments of the invention, the apparatus may comprise an ablation member for ablation of uterine tissue in the female mammal. Thus, the apparatus according to such embodiments may be used for performing a combination treatment including sterilisation and ablation of uterine tissue, e.g. to. This is particularly advantageous in cases where an ablation is performed as a primary treatment, such as for treatment of menorrhagia, which also necessitates a sterilisation treatment. The ablation member may be the inflatable member. Thus, no additional ablation means are required.

In embodiments of the invention, the apparatus may further comprise heating means provided on a proximal side of said at least one separation member for heating said tissue necrotising fluid, said heating means having a heat emitting portion and a heat receiving portion which in use of the apparatus are positioned in thermal contact with each other, and which are separable from each other.

By the division of the heating means into a heat emitting portion and a heat receiving portion which are separable, two units may be produced having each its own internal circuitry for heat and possibly other supplies. By such a division of the apparatus the heat production may be performed in one unit, which consequently contains the devices for this production, and the produced heat may be transmitted to the other unit. The unit receiving the produced heat may therefore be simplified in design and shielded off from internal contact with the other unit. Hence, the unit comprising the heat receiving portion may be liquid tightly separated from the unit comprising the heat emitting portion and there is no risk for contamination of the liquid by the contact with the unit comprising the heat emitting portion. The unit comprising the heat receiving means can be produced at low cost and therefore becomes better adapted to be disposed after use if desired. Another advantage is that the amount of liquid circulating enclosed in the apparatus becomes small, which reduces the heating up time and it has been tested that although the positioning of the heat emitting portion may be at a distance from the separation member the heat loss in the sterilisation lumen is in principle negligible. Yet another advantage is that the unit comprising the heat receiving portion is not by itself connected to any power unit and therefore the patient is at no risk of being subjected to electric shock.

In embodiments of the invention, the apparatus is separable into a reusable unit and a disposable unit, said disposable unit being adapted to be sterile.

In embodiments of the invention, the heat emitting portion is positioned in said reusable unit and said heat receiving portion is positioned in said disposable unit.

In embodiments of the invention, the reusable unit comprises a regulation unit.

In embodiments of the invention, the circulation assembly comprises a fluid compartment in fluid connection with said sterilisation lumen, a wall of said fluid compartment at least partly forming said heat receiving portion. This way a simple yet efficient structure is achieved.

In embodiments of the invention, the fluid compartment is connected to a proximal part of the sterilisation lumen via a fluid inlet opening and is connected to a distal part of the sterilisation lumen via a fluid outlet opening.

In embodiments of the invention, the fluid compartment has an at least partly conical shape, comprising a wider bottom portion and a narrower top portion as seen in a vertical direction. This way air enclosed in the necrotising fluid and/or the compartment will ascend to the top portion where it collects. Air drawn during treatment will also collect at the top portion. When air is seen it is visual proof that the fallopian tubes are generally free from fluid and it is also confirmation that no necrotising fluid is left in the oscillation lumen and that the volume of retracted necrotising fluid will be replace by a portion of the hot fluid in the compartment. Such "discarded" necrotising fluid would become lukewarm instead of hot since there would be an air pillar encapsulated in the liquid, thus hindering all liquid to come in contact with the heat receiving portion. The apparatus would as a result not perform well.

In embodiments of the invention, the fluid inlet opening in located near the base portion of the fluid compartment and the outlet opening is located at the top of the fluid compartment. When the necrotising liquid enters the compartment it hence enters close to the heat receiving portion and is thus immediately exposed to the heat and heated to the desired temperature.

In embodiments of the invention, the heating means are heated by any of the methods chosen from the group of electric resistance heating, induction heating, microwave energy heating, and semi-conductive ceramic elements, such as PTC elements.

In embodiments of the invention, the heat emitting portion is a tempered surface and is in use of the apparatus positioned in mechanical contact with the heat receiving portion.

In another aspect, the invention relates to a method for sterilisation of a female mammal, comprising the steps of:

(a) separating the tubal ostium of a fallopian tube from the uterine cavity of the female mammal;

(b) injecting a tissue necrotising fluid via an sterilisation lumen at a position which is in communication with said fallopian tube; and (c) regulating said tissue necrotising fluid to circulate within said sterilisation lumen and said fallopian tube.

The method of the invention allows simple, safe and reliable sterilisation of the female mammal. The method does not require advanced medical training to be performed correctly, nor extensive surgical or other medical equipment. Furthermore, by injecting and circulating a tissue necrotising fluid occlusion of the fallopian tube is achieved through the formation of scar tissue at the necrotised area, thus avoiding the use of a foreign object, such as a plug, which might be dislocated due to spasms of the fallopian tube. The step of circulating the tissue necrotising fluid allows maintenance of the tissue necrotising effect for a desired period of time.

The step of separating said fallopian tube from said uterine cavity may typically comprise inflation of an inflatable member by introduction of an inflation fluid into the inflatable member.

Both fallopian tubes of a female mammal may be simultaneously separated from said uterine cavity.

In embodiments of the invention, steps (b) and (c) of the method may be performed on each fallopian tube separately. Thus, it is possible to treat only one of the fallopian tube, or at least to treat one fallopian tube at a time. Treatment of only one fallopian tube may be desirable e.g. if the other fallopian tube has been found to be naturally closed. Alternatively if one or both of the fallopian tubes is/are partially closed they may require different regulation, e.g. of injection volume or injection speed, in order to achieve said injection and/or circulation.

Typically, the tissue necrotising fluid before injection thereof into the fallopian tube may be heated to a temperature of 65-180° C., and preferably 75-90° C. Thus, necrotisation of tissue may be achieved by cauterization. The tissue necrotising fluid may comprise a fluid selected from the group consisting of: sterile water, saline, glycerine, glucose, mannitol, glycerine based liquids, and combinations thereof. These fluids may be, as such, harmless to the tissue of the female mammal, such that spill of fluid of ambient temperature into the abdominal cavity would not cause damage.

In embodiments of the invention, the method may comprise, before step (c), a step (b1) of injecting a fluid into the fallopian tube via said sterilisation lumen and monitoring a fluid pressure within the sterilisation lumen for determining whether the fallopian tube is open or closed. If a fallopian tube is partially closed it may require a different regulation, e.g. of injection volume or injection speed in order to achieve said injection and/or circulation of tissue necrotising fluid. Furthermore, if a fallopian tube is found to be fully closed, it may not require a sterilisation treatment at all.

In further embodiments, the method may further comprise the step of ablating uterine tissue in the female mammal. This is particularly advantageous in cases where an ablation is performed as a primary treatment, such as for treatment of menorrhagia, which also necessitates a sterilisation treatment. The sterilisation and uterine ablation treatments may be performed simultaneously or consecutively. The step of ablating uterine tissue may be performed using said inflatable member.

BRIEF DESCRIPTION OF THE DRAWINGS

The present invention is in the following described with the aid of the accompanying drawings, which are merely included as non-limiting representations of some preferred and contemplated embodiments.

FIG. 1b shows a sterilisation catheter also shown in FIG. 1a,

FIG. 1c shows the sterilisation catheter of FIG. 1b partly in cross section,

FIG. 1g shows parts of the sterilisation apparatus according to the invention, in particular the connector and the syringes, FIGS. 1h and 1i show in cross section alternative embodiments of the circulation assembly, FIG. 7 shows a schematic diagram of a pulsation sequence used in the sterilisation method according to the invention, FIG. 8 shows an alternative embodiment of the sterilisation apparatus designed to perform simultaneous sterilisation and ablation of uterine tissue, FIG. 8b is a cross-section taken along the line C-C of FIG. 8, FIG. 10a shows in top view a compartment and syringes of FIG. 9, FIG. 10b shows in cross-sectional view along A-A of the connector of FIG. 10a, FIG. 10c shows in side view the connector of FIG. 10a, FIG. 11 shows in partial cut view the catheter of FIG. 9, FIG. 12a-e show a cross-section of the connector, sterilisation lumen and parts of a uterus and fallopian tube of a patient during a treatment sequence according to the invention, and FIG. 13a-b show cross-sections of parts of the uterus, fallopian tube and of a balloon according to the invention.

DETAILED DESCRIPTION OF A PREFERRED EMBODIMENT OF THE INVENTION

Throughout this application the words distal and proximal, respectively, are intended to refer to a situation as seen in relation to an operator or a user of the sterilisation device.

Figure 1A:
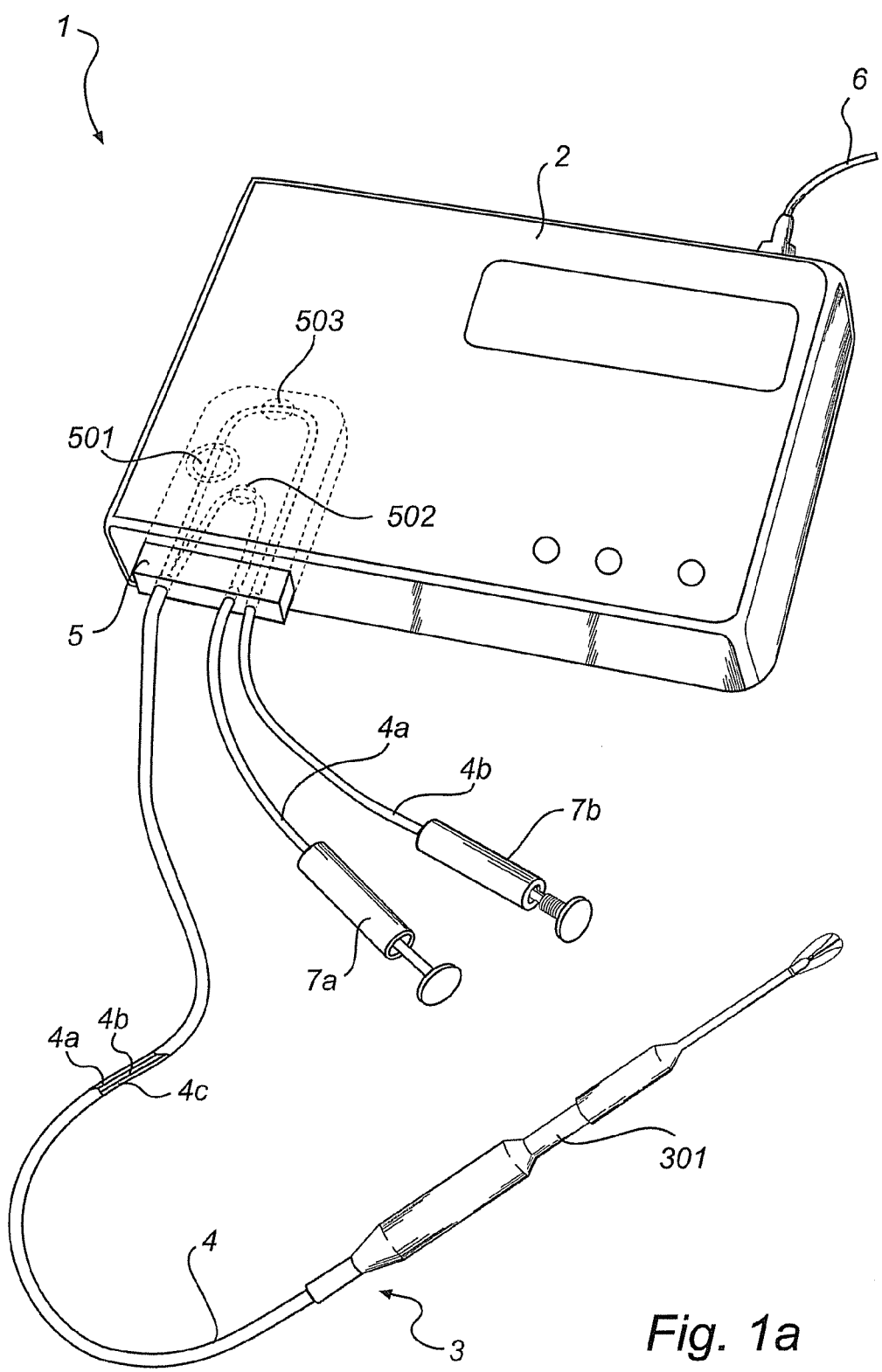
FIG. 1a shows a sterilisation apparatus according to the invention.

Referring now to FIG. 1a, a sterilisation apparatus 1 according to embodiments of the invention is shown comprising a sterilisation catheter 3 which comprises a balloon catheter 301, a conduit 4, a connector 5, a first fluid lumen 4a, a second fluid lumen 4b, and a third lumen 4c (for electrical wires). The lumens 4a-c, in particular fluid lumens 4a, 4b, may be formed by separate tubes. However, where contained in the conduit 4, the lumens 4a-c may be cavities in the conduit 4. The first fluid lumen 4a is connectable to a first fluid injection syringe 7a with valves (see FIG. 1g), also called inflation syringe 7a. Similarly, the second fluid lumen 4b is connectable a second fluid injection syringe 7b with valves (see FIG. 1g), also called sterilisation syringe 7b.

The first and second fluid lumens 4a, 4b pass through the connector 5. The connector 5 is at least partly inserted in a regulation unit 2 and provides connection between the sterilisation catheter 3 and the regulation unit 2 and the syringes 7a and 7b, respectively. The first and second fluid lumens 4a, 4b both enter and exit, respectively, the connector at a part thereof readily accessible from the outside of the regulation unit 2. The regulation unit 2 comprises means for creating a back-and-forth movement of a first membrane 501 in the connector 5, which movement induces fluid pulses for circulation of fluid in the second fluid lumen 4b, and also comprises at least one fluid pressure sensor in mechanical connection with a second membrane 502 in the connector for measuring of the pressure in the first lumen 4a, and at least one fluid pressure sensor in mechanical connection with a third membrane 503 in the connector for measuring of the pressure in the second lumen 4b. Furthermore, the connector 5 has means for electrical connections between electrical wires contained in lumen 4c and said regulation unit 2. The regulation unit 2 provides, via said electrical wires, electrical energy to at least one heater positioned in the balloon catheter 301 for heating of fluid, and for controlling and regulating the temperature of said heater(s). The regulation unit 2 also includes all necessary computer processors for operating and controlling the sterilisation apparatus 1 and for performing the method of the invention using said apparatus.

In the embodiment shown in FIG. 1a the regulation unit 2 is connected by an electrical wire 6 to a 220 V, 50 Hz electrical system, but it is contemplated that other stationary electrical systems or mobile systems such as batteries could be used.

The sterilisation catheter 3 may comprise more than one first fluid lumen 4a, and/or more than one second fluid lumen 4b. The first and second fluid lumens, respectively, define separate fluid lumen paths. The first lumen 4a, also called the inflation lumen, provides an inflation fluid path from the inflation syringe 7a for injection of inflation fluid to the balloon catheter 301. Said inflation fluid path extends in the inflation lumen 4a from the inflation syringe 7a, passes the connector 5, and subsequently enters the balloon catheter 301 via the conduit 4. Fluid may travel along the inflation fluid path in both directions, i.e. in the inflation lumen 4a in the direction from the inflation syringe 7a towards the balloon catheter 301, or in the direction from the balloon catheter 301 towards the syringe 7a. Similarly, the at least one second lumen 4b, also called sterilisation lumen, provides a sterilisation fluid path from the sterilisation syringe 7b for injection of sterilisation fluid to the balloon catheter 301. The sterilisation fluid path extends in the sterilisation lumen 4b from the sterilisation syringe 7b, passes the connector 5 and a pulse mediator in the form of the membrane 501, and subsequently enters the balloon catheter 301 via the conduit 4. Fluid may travel along the sterilisation fluid path in both directions, i.e. in the direction from the sterilisation syringe 7b towards the balloon catheter 301 as described above, or from the balloon catheter 301 towards the sterilisation syringe 7b.

The fluid paths within the sterilisation catheter 3 will be explained in more detail below.

The sterilisation catheter 3 is sterile and as a whole or in parts may be made partly or fully reusable, or as a disposable article. According to this embodiment, the entire sterilisation catheter 3, including the balloon catheter 301, the conduit 4, the lumens 4a-c, the electrical wires provided in lumen 4c, and the heater 319 are disposable. Also, the syringes 7a and 7b are disposable.

Furthermore, the balloon catheter 301 and optionally other parts of the sterilisation catheter 3 may be made of one or more materials which is/are acceptable for contact with living tissue, in i.e. a material which does not induce adverse biological reactions of the living tissue upon contact for a time corresponding to the duration of the method described herein.

The details of the sterilisation catheter 3 will now be described with reference to FIGS. 1b-1i. FIG. 1b shows the balloon catheter 301 which forms part of the sterilisation catheter 3 which forms part of the sterilisation apparatus 1 from FIG. 1a.

The balloon catheter 301 comprises an elongated tubular body 304. In the proximal part is a handle 302 provided for the operator of the sterilisation apparatus 1. The middle and distal part of the balloon catheter comprises a tube containing at least one lumen (not shown). The outmost, distal part of the balloon catheter 301 comprises an elongation of said tube in the form of a pin 308 which is fixed to a balloon 307 at the inside wall of a distal part of the balloon 307.

A tubular shaft 305, also referred to as length adjuster, concentrically encompasses the middle and distal part of the tubular body 304 and can slide in a longitudinal direction in relation to the tubular body 304. The distal part 306 of the shaft is narrow to allow easy introduction into the uterus via the cervix and has a length bridging at least the length of the vagina and the cervix. The collar of the balloon is outwardly fixed to the distal part 306 of the shaft 305 in a fluid tight manner. By moving the shaft 305 in a longitudinal direction relative to the pin 308 the size of the balloon 307 can be adjusted. On the shaft 305 there is provided means (not shown) for fixation of the shaft to the tubular body.

The balloon 307 is made of a highly elastic and flexible material, such as silicone, allowing considerable expansion of the balloon e.g. by inflation.

Figure 1D:
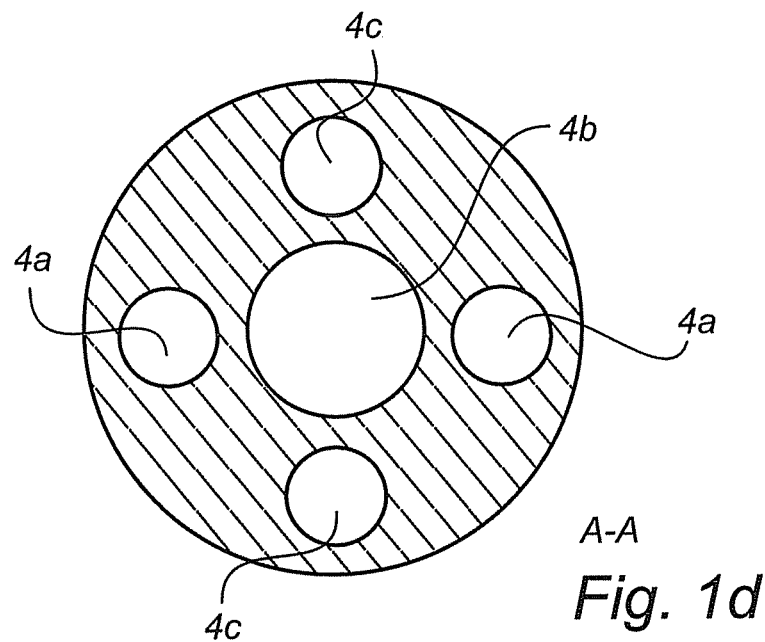
FIG. 1d is a cross-section taken along the line A-A of FIG. 1c.

FIG. 1c illustrates the balloon catheter 301 of FIG. 1b in cross-section, and FIG. 1d illustrates the conduit 4 in cross-section A-A of FIG. 1c. The two inflation lumens 4a, the centrally located sterilisation lumen 4b, and the wire lumens 4c exit the conduit 4 and enter the hollow balloon catheter 301 at the proximal end 303 of the handle 302 which contains a heating compartment 312 comprising a heater 319 which is electrically powered by means of electrical wires contained in wire lumen 4c. The fluid lumens 4a and 4b subsequently pass through the tubular body 304 and the shaft 306 and arrive at the distal part of the balloon catheter 301. In the embodiment shown in FIGS. 1b and 1c, two inflation lumens 4a are provided for inflation of the balloon 307. Having entered the handle 302, the inflation lumens 4a pass outside the heating compartment 312 and between said heating compartment 312 and the wall of the balloon catheter 301 and through the shaft 306 to the distal part of the balloon catheter 301, where the inflation lumens 4a debouch into the balloon 307 via openings (not shown in FIGS. 1b and 1c; see FIG. 1f). The inflation lumens 4a form part of a closed, pressurized inflation system intended for inflation of the balloon 307 by means of a fluid, e.g. a gas, such as air, or a liquid, such as water or saline.

Furthermore, as illustrated in FIG. 1c, a sterilisation fluid lumen 4b is provided for injection and circulation of sterilisation fluid. The sterilisation lumen 4b, having entered the handle 302 at the proximal end 303, debouches into said heating compartment 312 for heating of sterilisation fluid. On the distal side of the heater 319, the sterilisation lumen 4b branches into two initially parallel, preferably flexible, sterilisation lumens 4b', each one arranged in a rigid tube 313 which leaves the heating compartment 312 and continues through the distal part of the balloon catheter 301 into the balloon 307.

Close to the handle 302, opposing channels 314 ending in openings are provided in the wall of the tubular body 304. Corresponding openings 315 are provided in the respective walls of the tubes 313, which is explained in detail in connection with FIG. 1e, which enable alternately blocking the provision of fluid to each sterilisation lumen 4b' by means of a clamping device 316 so that fluid may pass through only one sterilisation lumen 4b' at a time. Thus, treatment of only one fallopian tube at a time may be performed.

The two sterilisation lumens 4b' leave the tubes 313 in the balloon in the form of two flexible tubes of fine calibre. The sterilisation lumens 4b' debouch at the outer face of the balloon 307 via debouching openings 309 as shown in FIG. 1c. The sterilisation lumens thus create fluid paths from the sterilisation syringe 7b to the atmosphere surrounding the balloon 307. The fluid within the sterilisation lumen 4b is never in contact with the inner atmosphere of the balloon 307, which may comprise an inflation fluid inside the balloon 307. The sterilisation lumens 4b' are attached to the balloon 307 at their respective debouching openings 309. The sterilisation lumen(s) form(s) part of an open injection system for injection, circulation and optionally retraction of sterilisation fluid in the fallopian tubes.

Hence, the sterilisation fluid circulation system, which also comprises sterilisation syringe 7b, is separate from the closed inflation system, and there is no fluid communication between these systems.

Figure 1E:
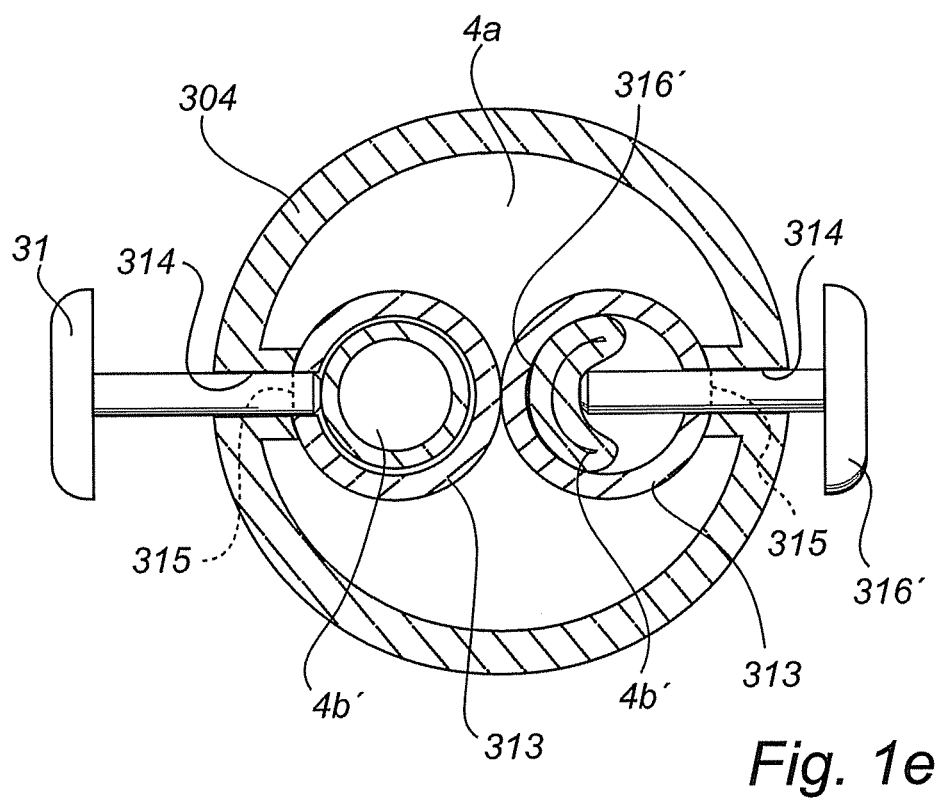
FIG. 1e is a cross-section taken along the line B-B of FIG. 1c.

FIG. 1e shows a cross sectional top view of the balloon catheter taken along the line B-B of FIG. 1c. The two sterilisation lumens 4b' are enclosed in respective tubes 313, which are enclosed by the wall of the tubular body 304. The wall of the tubular body is provided with opposing channels 314 ending in openings in the wall, and the rigid tubes 313 are provided with corresponding openings 315 arranged in line with the respective openings 314. The openings 314 (and the corresponding openings 315) may also be arranged on the same side of the tubular body 304, i.e. not in opposing position, or in any other suitable position. The purpose of the openings 314, 315 is to allow a clamping device 316 to reach from the exterior of the balloon catheter through the walls of the tubular body 304 and the rigid tube 313 to constrict the flexible sterilisation lumen 4b'. In FIG. 1e, a clamping device 316' is in clamping position, thus blocking the passage of fluid through the corresponding sterilisation lumen 4b'. Another clamping device 316 is in an unclamping position, allowing the passage of fluid though the sterilisation lumen. Hence, provision of fluid through only one of the sterilisation lumens 4b' at a time may be achieved. The clamping devices 316, 316' may be operated manually by the operator of the sterilisation apparatus.

Figure 1F:
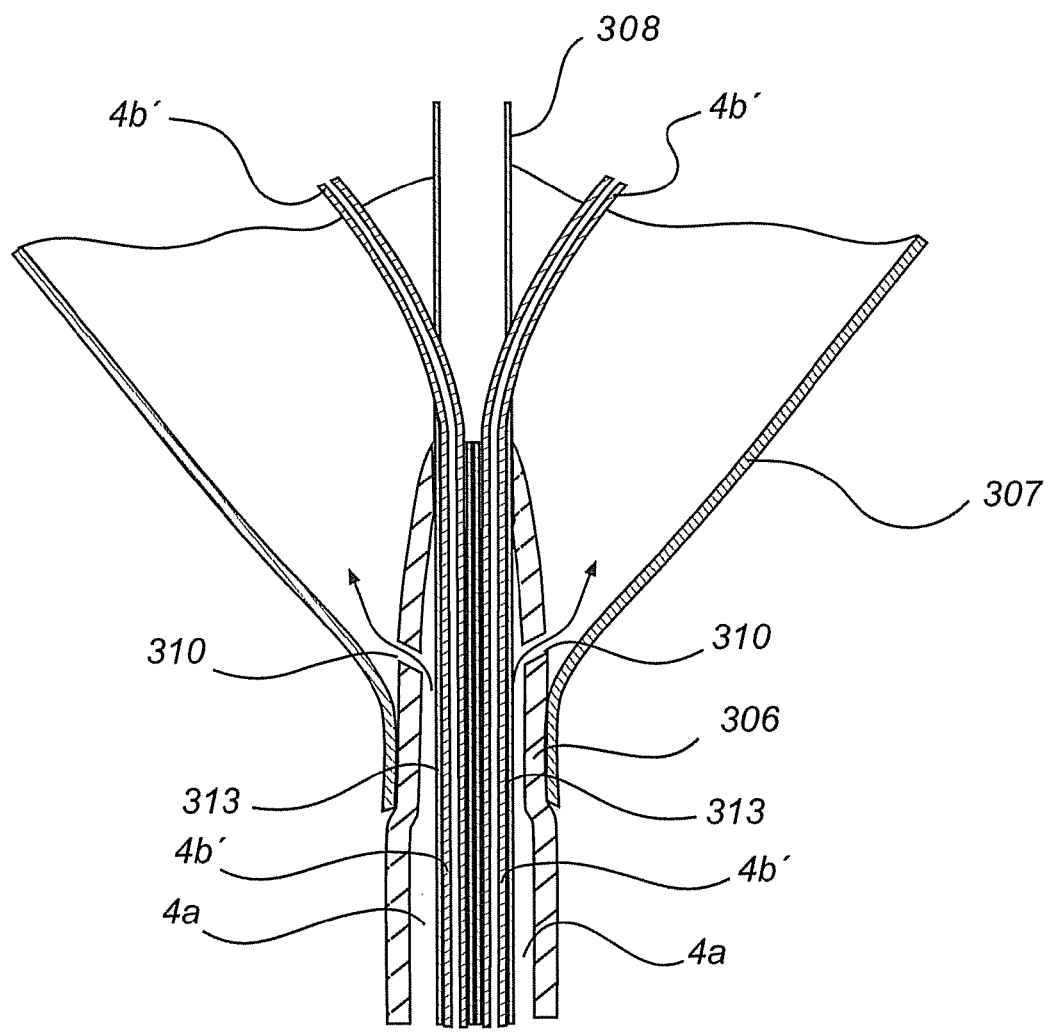
FIG. 1f is a close view of parts of the sterilisation catheter shown in FIGS. 1b and 1c.

FIG. 1f shows a cross-sectional close view of the balloon catheter 301 at the point of attachment of the balloon 307 to the shaft 306 as shown in FIG. 1c. In the shaft 306, which is hollow, the two tubes 313, each containing a sterilisation lumen 4b', extend some distance into the balloon 307 to a point where the two flexible sterilisation lumens 4b' are separated, finally debouching at the outer face of the balloon (not shown in this figure). The diameter of each of the lumens 4b' may be about 0.5-1 mm. As described above, the sterilisation fluid may pass in both directions through the sterilisation lumen 4b/4b'. The inflation lumens 4a, which are provided radially outside the tubes 313, end in the form of openings 310 some distance into the interior of the balloon 307. Arrows indicate the direction of fluid movement during inflation of the balloon 307. Naturally, during deflation of the balloon 307, the direction of the fluid movement is opposite to the arrows in the figure.

FIG. 1f also shows part of the length adjustment pin 308, which may be solid, or hollow.

FIG. 1g-i show how the circulation of sterilisation fluid described herein may be achieved by means for creating a back and forth movement located in the regulation unit 2 acting on the connector 5. FIG. 1g illustrates parts of the lumens 4a, 4b and the connector 5 which comprises a preformed flexible membrane 501 connected to the sterilisation lumen 4b. Within the connector 5, lumens 4a and 4b may be preformed channels in the connector.

FIGS. 1h and 1i show cross-sectional side views of the connector 5 and the membrane 501. The sterilisation lumen 4b debouches into a cavity formed by the body of the connector 5 and the membrane 501, such that the fluid passing through the sterilisation lumen 4b may fill the volume under the membrane 501. As illustrated in FIG. 1h the membrane may be compressed for example by a rotating cam 201 and, when released from compression, go back by its own force or by a spring (not shown). In another embodiment, illustrated in FIG. 1i, a linear motor is used to periodically push and pull the membrane between expanded and compressed positions. The movement of the membrane creates a controlled volumetric pulsation of the sterilisation fluid through the sterilisation lumen(s) 4b/4b' and the fallopian tubes, which is important for performing efficient treatment and which will be explained in more detail below. It is preferable that when the pulsation is stopped the membrane takes its compressed position, which will also be explained in more detail below.

Figure 2:
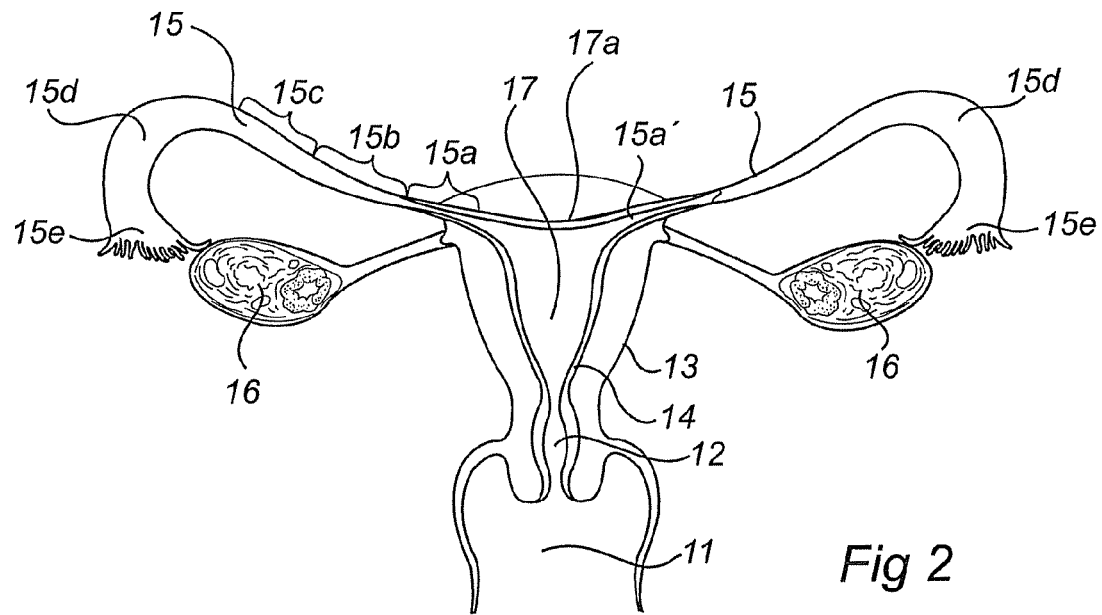
FIG. 2 shows the major elements of the female reproductive system.

FIG. 2 shows a schematic view of the major elements of the female reproductive system. Reference numeral 11 denotes the vagina, 12 the cervix, 13 the uterus, 14 the endometrium of the uterus 13, 15 the two fallopian tubes and 16 the ovaries. 17 denotes the uterine cavity. 17a denotes the fundus, which is the upper wall of the uterine cavity 17. The two fallopian tubes 15 connect the uterine cavity 17 with the two ovaries 16. The entrance region of the fallopian tube 15 from the uterus is called the tubal ostium 15a'. The section of the fallopian tube next to the tubal ostium 15a' is called the intramural section 15a which leads through the uterine wall and is approximately 10 mm in length and has an inner diameter of about 1 mm. The next section of the fallopian tube 15 is the isthmus 15b. Beyond the isthmus portion there is a considerable increase in the fallopian tube lumen. Next to the isthmus is the ampulla 15c, further on is the infunddipulum 15d, and finally, in close connection to the ovary 16 is the fimbriac 15e. In its natural state the uterus 13 is flat and has a slightly triangular shape.

Figure 3A:
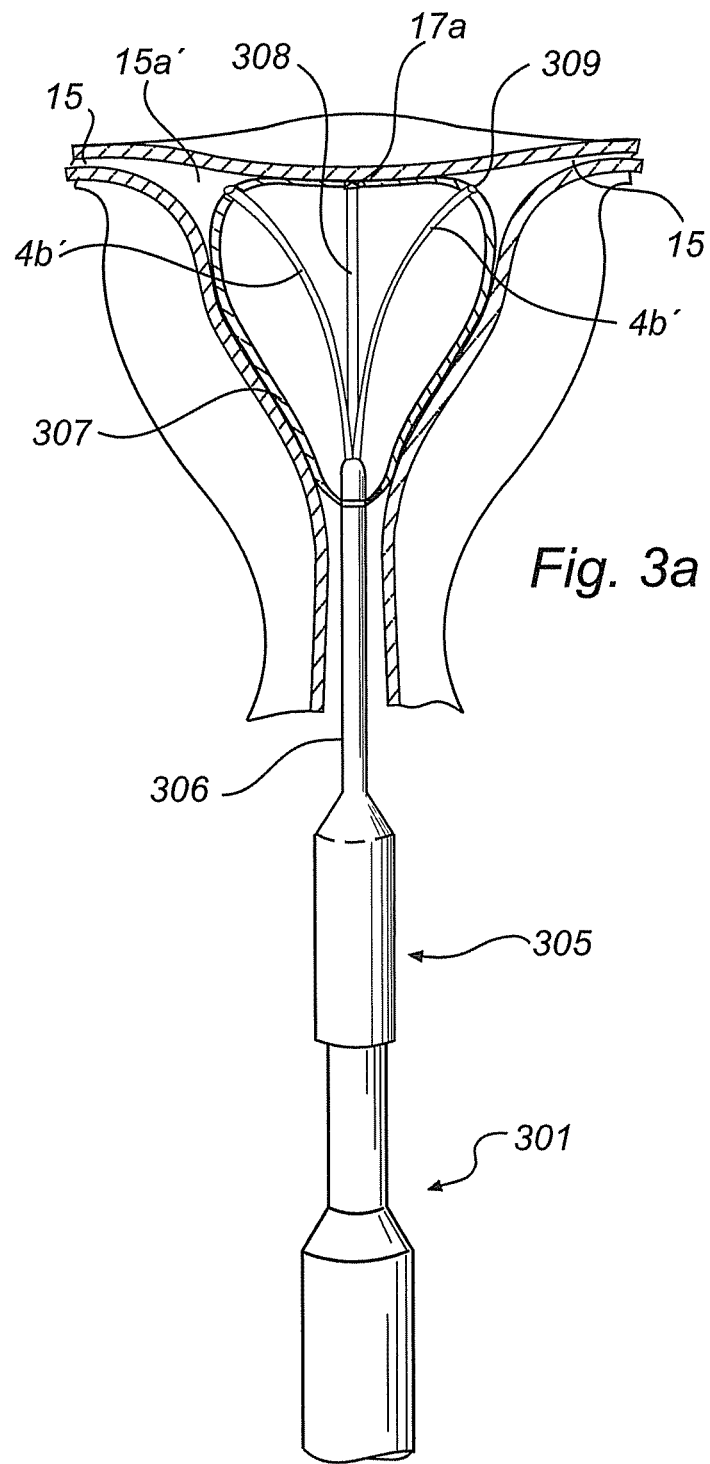
FIG. 3a shows the balloon catheter of FIG. 1a positioned in the uterine cavity.

FIG. 3a shows an inflated sterilisation device 3 when in use and installed in the uterine cavity 17.

The sterilisation method will now be described with reference to FIG. 3a, which shows the balloon catheter inserted and inflated, and FIG. 1g to which reference has already been made. In preparation for the insertion, the operator has measured the length of the uterine cavity e.g. by a sound in order to be able to suitably adjust the length of the balloon 307 by utilising the shaft/length adjuster 305. Before insertion, the sterilisation lumen 4b may be at least partly filled with sterilisation fluid, which is performed by filling the syringe 7b with sterilisation fluid, connecting the filled syringe 7b (FIG. 1g) to the sterilisation lumen 4b, opening a valve 8b (FIG. 1g) and injecting from the sterilisation syringe 7b a desired volume of fluid into the sterilisation lumen 4b. The balloon catheter 301 has been inserted into the uterine cavity with the balloon 307 uninflated. As the uterine cavity is triangular and relatively flat the balloon catheter should be inserted so that the plane constituted by the two sterilisation lumens 4b' and the pin 308 when the balloon is inflated essentially coincides with the plane constituted by the fallopian tubes. The distal end of the length adjustment pin 308 should when installed abut the fundus 17a of the uterine cavity. The need for accuracy of the placement of the debouching openings 309 is not very high since the balloon 307 when inflated should seal off each fallopian tube 15 properly.

The inflation balloon 307 has been inflated by filling the syringe 7a (FIG. 1g) with an inflation fluid, connecting the syringe 7a to the inflation lumen 4a, opening a valve 8a (FIG. 1g) and subsequently injecting a suitable volume of the inflation fluid via the inflation lumen 4a into the balloon 307 as shown in FIG. 1e, and finally closing the valve 8a.

The main reason for inflation of the balloon 307 within the uterus 13 is to create a temporary sealing of the fallopian tubes 15 from the rest of the uterine cavity 17. The inflation pressure within the inflatable balloon 307 and the balloon wall thickness must thus be of a magnitude such that the sterilisation method can be performed with only little or no leakage of the sterilisation fluid into the uterine cavity 17, or from one fallopian tube to the other. The pressure is given by the sensor 502. A pressure within the balloon 307 of approximately 140-240 mmHg is sufficient under normal conditions to achieve the desired sealing of the fallopian tube from the uterine cavity. Furthermore, a high pressure allows a better penetration of the sterilisation fluid in the case of resistance of the fallopian tube. This will be further elucidated below.

Before proceeding to the sterilisation, it may be necessary to establish whether each fallopian tube 15 is open, or if it is partially or fully closed. A partially closed tube 15 may be difficult to securely detect as open. The device according to embodiments of the invention can also be used as a diagnostic device replacing the use of devices presently used for examination in case of fertility problems. The open or closed state of the fallopian tubes may be determined by injecting through the sterilisation lumens 4b' a fluid which is harmless to the body, such as sterile saline of 37° C. If there is no occlusion of the fallopian tubes 15 there will be no or only little resistance to the injection of the fluid. However, if a fallopian tube resists the insertion of fluid, a pressure is built up in the sterilisation lumen(s) 4b, 4b' which can be detected and monitored by the regulation unit 2, if it is provided with a pressure sensor and a corresponding third membrane 503 (FIG. 1g) in the connector. The regulation unit 2 (FIG. 1a) may be adapted to measure the pressure over time, and if the built-up pressure drops with a certain speed or below a certain level it may be assumed that the fallopian tube is open and that a sterilising treatment can be performed. Only a small amount of fluid is required in order to detect whether a fallopian tube 15 is open or closed as described above. Furthermore, if there is a plug in the fallopian tube it may be pushed out by running the pressurised fluid pulsating system at ambient or high temperature.

Figure 3B:
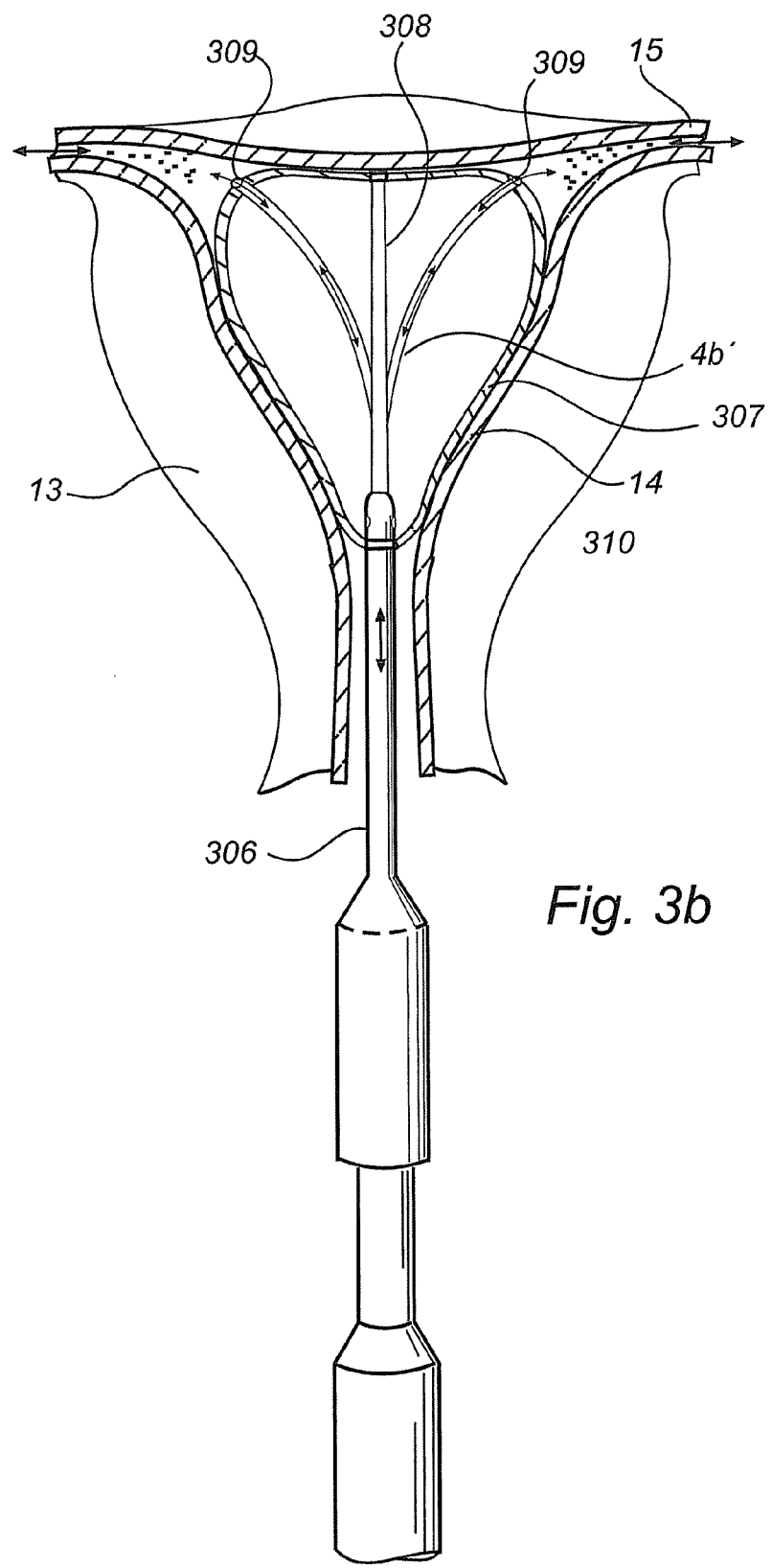
FIG. 3b shows the sterilisation device of FIG. 1a during a sterilisation procedure according to the present invention.

FIG. 3b shows the step of sterilisation of both fallopian tubes 15 simultaneously or separately. Having determined that both fallopian tubes 15 are open as described above, a sterilisation fluid, which preferably may also serve as a contrast fluid, such as sterile saline, is injected into each fallopian tube 15 via the sterilisation lumens 4b'. Preferably a quantity of sterilisation fluid is injected in order to completely fill the fallopian tubes and even cause a spill of fluid into the abdomen, which in this case is harmless since the fluid is not hot. Thereafter the sterilisation syringe is pulled back corresponding to an amount of about 0.2-0.3 ml to prevent the risk for spill of hot fluid into the abdominal cavity during the treatment. Preferably the membrane 501 should be in compressed state when the driving mechanism is stopped. Next, the circulation of the sterilisation fluid is started. When starting, the membrane 501, thanks to its position in a compressed state, is withdrawing sterilisation fluid from the fallopian tubes. The reason for such an initial back stroke is that, as described above, during filling of the fallopian tubes with sterilisation fluid, some fluid might spill over into the abdomen of the patient. Therefore the initial back stroke eliminates more spillage. This can be achieved by utilising a stepper motor as the driving mechanism of the membrane 501. The stepper motor operates the rotating cam 201, which has been described in connection with FIG. 1h, such that when the stepper motor is stopped, the rotating cam 201 is leaving the membrane 501 in a compressed state. When again starting the stepper motor the membrane 501 starts by a back stroke and hence at least to a certain predetermined degree withdraws the sterilisation fluid from the fallopian tubes.

As a next step the sterilisation fluid is heated to the desired temperature while the fluid is pumped back and forth into the fallopian tubes by means of the movement of the membrane 501 of the connector 5. For each back stroke some of the sterilisation fluid is retracted from the fallopian tubes into the heating compartment 312 and mixed with hot fluid contained therein. For each forth stroke, some of the hot sterilisation fluid in the heating compartment is pushed via the sterilisation lumens 4b' into the fallopian tubes to a certain depth. During this heating-up period, the heater will produce enough heat to cover heat losses and provide an increase in temperature of the sterilisation fluid, thus increasing the temperatures of the inside of the tubal ostium and fallopian tubes. The desired temperature in order to achieve sufficient necrotisation of the tubular tissue in a short time is 75-90° C. if water or a water-based liquid is used. After a short time of pumping back and forth, a temperature steady-state is achieved, meaning that the power in the form of heat delivered from the heater balances the heat loss during transportation to the fallopian tubes, and heat loss in the fallopian tubes (mainly caused by the blood circulation). The necessary regulation of sterilisation fluid temperature and treatment time may be automatically set by the heating system. During the procedure the penetration (depth) of the treatment into the fallopian tube can be changed e.g. by adjustment of the circulated amount of sterilisation fluid on the sterilisation syringe.

The time required for effective sterilisation may be different and depending on many factors. For example, sterilisation temperatures in the range of 70-90° C. obtained with water based liquids and maintained for 4-12 minutes may be sufficient. Alternatively, non-water based liquid may be used, such as a glycerine based liquid, in order to achieve a sterilisation temperature above the boiling temperature of water, e.g. of 150-180° C. By using such a high sterilisation temperature, the treatment time may be reduced considerably.

After the sterilisation procedure according to any one of the disclosed embodiments has taken place, the sterilisation fluid is retracted, the inflation fluid within the inflation balloon 307 is removed such that the balloon 307 is deflated, and the balloon catheter 301 is completely removed from the patient.

The aim of the present invention is to create occlusion of a part of the fallopian tube by necrotisation by heat. It is known that the application of heat generated by an electric device can cause irreversible damage of the mucosal layer of the fallopian tube. If a part of the underlying muscular layer is affected too there will be a radial shrinkage of the tissue resulting in scarification. The necrotisation promotes fibroblastic proliferation from the muscular layer and the formation of scar tissue leads to occlusion of the fallopian tube.

It is however important that the tissue is treated over a significant length to ensure 100% occlusion. As it is difficult to promote shrinkage in the intramural portion, it would be preferable to treat the isthmus region. According to the different embodiments of the invention the desired parts of the fallopian tube may be treated by a simple regulation of the amount of sterilisation fluid. If by mistake too much sterilisation fluid is injected there would be a risk of spill into the abdomen. However, as the diameter of the fallopian tube is considerably larger beyond the isthmus these parts of the fallopian tube would serve as a buffer for the excess fluid.

Figures 4A, 4B:
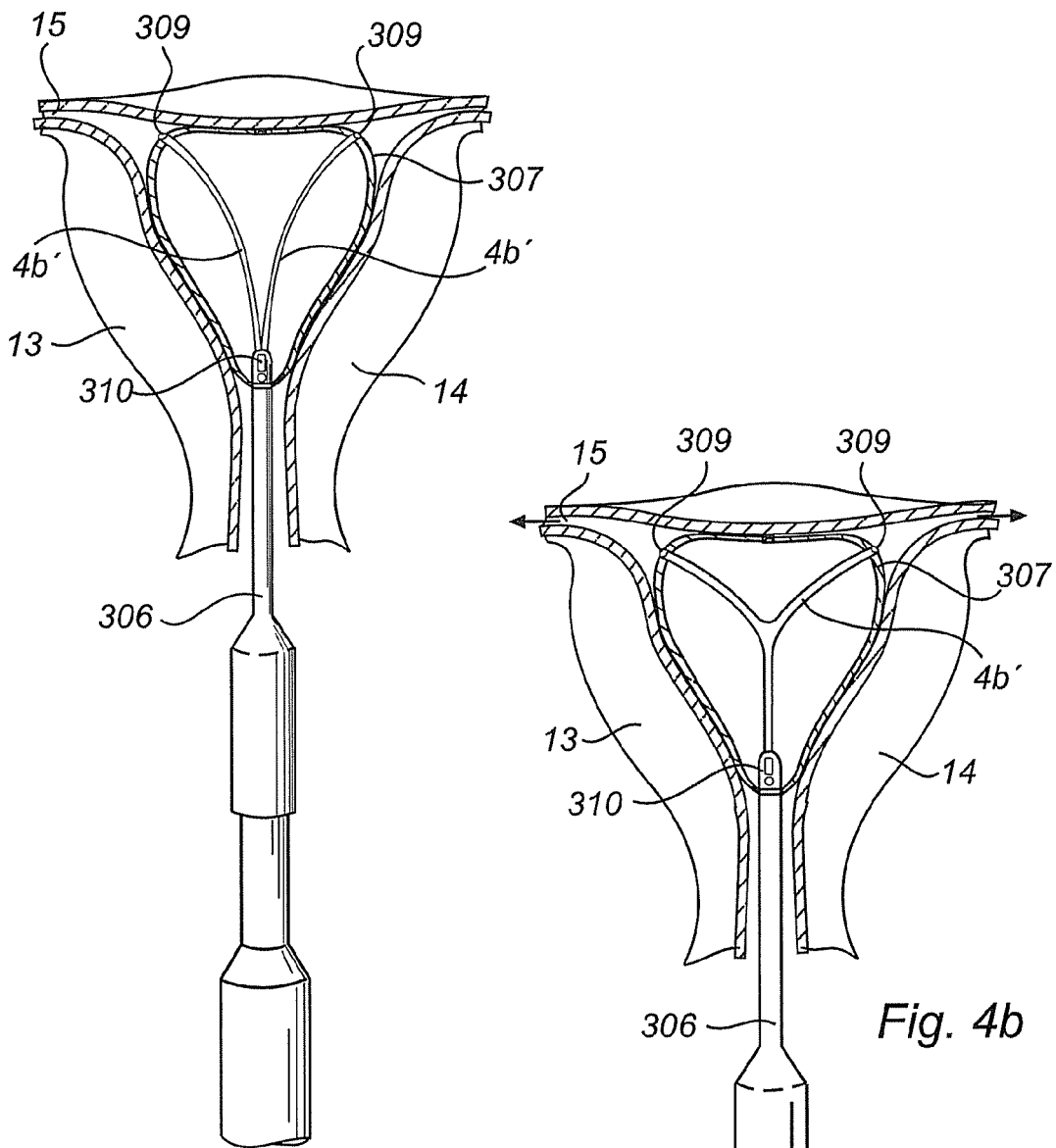
FIG. 4a shows an alternative embodiment of the sterilisation apparatus according to the invention.
FIG. 4b shows an alternative embodiment of the sterilisation apparatus according to the invention.

A further embodiment of the sterilisation device according to the invention is illustrated in FIG. 4a. As can be seen in this figure, the balloon catheter 301 lacks a length adjustment pin. Instead, to properly position the balloon catheter in the uterine cavity, the balloon catheter 301 may be inserted some distance into the uterine cavity, but not to abut the fundus. Next, the balloon 307 may be inflated as described above, and due to the shape of the balloon 307 the debouching openings 309 will then be adequately positioned in the lengthwise direction.

In FIG. 4b a further embodiment of the balloon catheter 301 is shown which also does not have a length adjustment pin 308. Further, the sterilisation lumen 4b is a single lumen up to a branching point within the inflation balloon 307, where it branches off into a V-shaped two lumen system, one lumen 4b' for each debouching opening 309.

In embodiments of the invention, each debouching opening 309 may comprise a plurality of openings, e.g. arranged in an array or in any two-dimensional pattern, such as a circle or circles. A plurality of openings at the end of each sterilisation lumen 4b' reduces the risk of insufficient injection of fluid into the fallopian tube in case the balloon catheter 301 is not perfectly positioned for the openings to match the tubal ostia.

In an alternative embodiment, the sterilisation device may comprise an alternative sterilisation lumen system. According to this embodiment, each sterilisation lumen 4b' comprises two lumens, one concentrically positioned within the other. An outer lumen is used for introducing fluid into the fallopian tube. An inner lumen is used for recovering said fluid from the fallopian tube. In this way, a circulation system is created which reuses in a simple manner the remaining heat from the retracted fluid to heat the fluid to be injected or at least to prevent further heat loss therefrom.

In another alternative embodiment of the sterilisation apparatus, a further heater in the form of a heating spiral may be positioned wound around each distal end of the sterilisation lumens in close proximity to their respective debouching opening. Such heaters could also include a radio frequency electrode, or other known heating devices. These further heaters can be used when either the heating capacity of the heater 319 and/or a heat loss preventing effect of the inflation fluid of the inflation balloon is not sufficient.

Figure 5A:
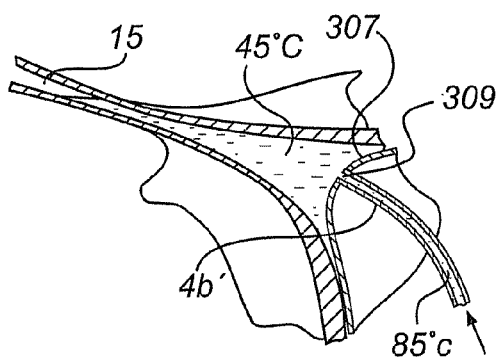
FIG. 5a-b show in cut view the cornual region and the intramural section of a fallopian tube during the heating up step of the sterilisation method according to the invention.
Figure 5B:
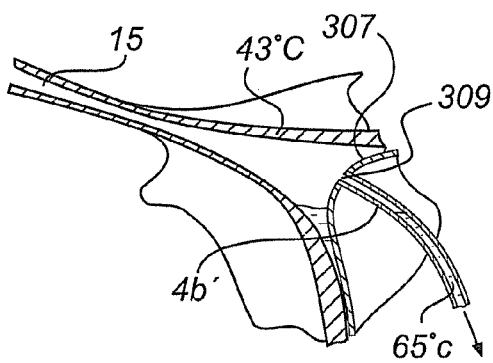

In order to fully disclose the sterilisation method according to the invention attention is now directed towards FIGS. 5a-b and 6a-b. FIGS. 5a and 5b show a sterilisation lumen in use during the heating up period described above. The balloon 307 is positioned in the uterine cavity (corneal region shown) so that the sterilisation lumen 4b' debouches in the proximity of the tubal ostium. FIG. 5a shows how an amount of sterilisation fluid of 85° C. has been injected by a forth stroke to fill the space delimited by the pressurised balloon and the intramural and the isthmus portions of the fallopian tube. The injection is fast as the fluid is forced by the volumetric forth stroke of the membrane 501 (FIG. 1g), which pulsates at a predetermined frequency which can be regulated. Due to the small dimensions of the fallopian tube and the sterilisation lumen 4b', only a small volume of sterilisation fluid is required to fill the desired part of fallopian tube. This volume may be properly adjusted using the fine tuning of the sterilisation syringe. The depth of the fluid injected into the fallopian tube may be controlled and monitored e.g. using ultrasound during treatment. The hot fluid stays in said space for a short period of time, thus heating up the lining of the fallopian tube.

FIG. 5b shows the back stroke by which a portion of the sterilisation fluid having a lower temperature of about 65° C. being pulled back into the heating compartment. The returning portion is by turbulence instantaneously mixed with the hot fluid in the heating compartment, the hot fluid in the heating compartment preferably having a volume which is larger than the small amount that is pulsated. The temperature of the fluid in the heating compartment may be kept at a temperature slightly above the desired treatment temperature and may be automatically maintained at that temperature by the heating system.

Figure 6A:
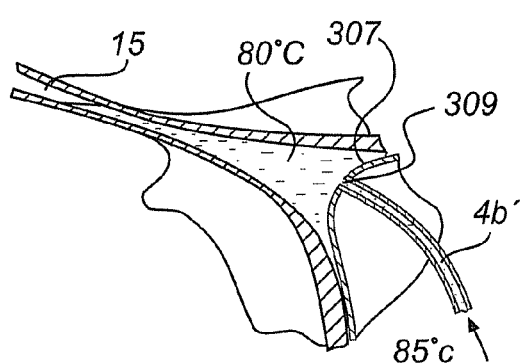
FIG. 6a-b show in cut view the cornual region and the intramural section of a fallopian tube during the sterilisation method according to the invention.
Figure 6B:
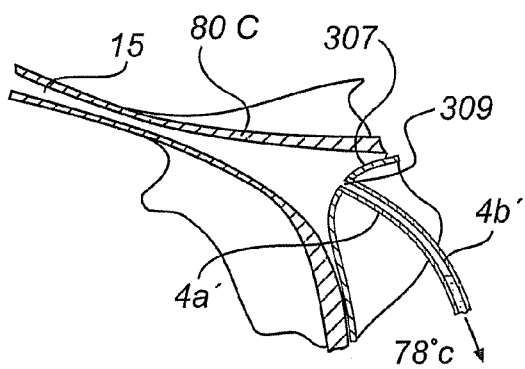

The temperature of the fallopian tube will increase gradually during the following pulse strokes. After some time of pulsation a steady state is reached. The steady state is illustrated in FIGS. 6a and 6b. The temperature of the inner surface of the fallopian tube is kept at the desired temperature, in this example 80° C., and the heat losses mainly caused by the cooling of blood circulation in the tubal ostium and the fallopian tube are compensated by bringing new hot fluid from the heating compartment to the ostium space (the forth stroke, FIG. 6a) and then retracting approximately the same amount of fluid having a lower temperature back to the heating compartment (the back stroke, FIG. 6b).

The total amount of time needed for the heating and sterilisation steps depends on the temperature of the injected sterilisation fluid, the power of the heater 302, the steady-state sterilisation temperature desired, the amount of sterilisation fluid used, how far into the fallopian tube 15 necrotisation should occur, and the amount of time required to perform a proper sterilisation at the desired sterilisation temperature. Typically, the heating and sterilisation steps would have a total duration of approximately 4-12 minutes if a sterilisation temperature of 70-90° C. is used.

In order to achieve efficient heating of the tissue, the time spent by a volume of the sterilisation fluid injected in the fallopian tube preferably exceeds the time spent mixing the volume of sterilisation fluid in the heating compartment. Thus, during pulsation, the time period from injection to retraction is typically longer than the time period from retraction to the next injection. This may be determined by the configuration of the cam illustrated in FIG. 1h.

FIG. 7 shows a schematic diagram with time on the x-axis and with the same activities as in FIGS. 6a and 6b. On the y-axis are the two positions A and B, where A corresponds to the fluid volume injected into the tube 15 (forth stroke) and B corresponds to the fluid pulled back. Each consecutive step is marked as a point called 1, 2, 3 etc. In the first step from 1 to 2, sterilisation fluid is injected to fill the sterilisation lumen, the uterine cornu and the fallopian tube 15 up to the desired level or depth, i.e. position A, corresponding to a time period $\Delta t_1$. In step 2 to 3 the fluid rests for a time period $\Delta t_2$ in order to heat the lining of the tube 15. At point 3 the retraction of fluid starts to again reach position B, i.e. the step from 3 to 4, corresponding to a time period $\Delta t_3$. During the step from 4 to 5, resting in position B, the fluid is heated for a time period $\Delta t_4$. A pulsation cycle is then complete and a new cycle starts The sterilisation sequence continues with the same pulsation cycle until a proper sterilisation has been performed. As can be seen in the diagram the steps from 1 to 2, from 3 to 4 and from 4 to 5 correspond to time periods $\Delta t_1$, $\Delta t_3$ and $\Delta t_4$ devoted to the transport of heat energy in the form of hot fluid from the heating compartment to the fallopian tubes while the time period $\Delta t_2$ is devoted to delivering energy for destruction of tissue.

The time efficiency, $t_{\mathit{eff}}$, of the heating by pulsating according to the invention can be expressed as $$t_{\mathit{eff}} = \Delta t_2 / (\Delta t_1 + \Delta t_2 + \Delta t_3 + \Delta t_4)$$

and it is desirable that the efficiency is high, as explained earlier. Preferably the value of $t_{\mathit{eff}}$ would be about 0.5 or more. As already mentioned, the time for each cycle can be adjusted by changing the pulsation frequency of the membrane 501. A higher frequency of the pulsation shown in FIG. 7 will reduce the time for each cycle but not change the time efficiency. It is however also desirable to shorten $\Delta t_1$ and $\Delta t_2$ for the transportation of hot fluid back and forth as the heat losses depend on velocity during transport.

As already mentioned above, the volumes of sterilisation fluid pushed back and forth are very small. As an example the volume of space between the balloon wall and the tubal ostium could be about 0.1-0.3 ml. The intramural part 15a of the fallopian tube may be 1 mm in length and have a volume of 0.01 ml. The volume of the isthmus 15b may be about 0.1-0.3 ml. Preferably, each sterilisation lumen 4b' would have an inner diameter about 0.6-1.0 mm and a volume measured from the debouching end at the balloon wall to the heating compartment of about 0.1-0.4 ml. The mean value of the total amount of fluid filling the space from the heating compartment to the end of the isthmus would be about 0.3-0.7 ml, but also larger volumes are possible. Consequently the amount of fluid to be pushed back and forth by the membrane would be about the same that filling the volume of the cornu and the intramural section of the fallopian tube in order to achieve a total exchange of fluid, although this is not necessary.

The pulsation frequency can preferably be from about 3 seconds per stroke (⅓ stroke per second) up to 10 strokes or more per second, for example about 1 stroke per second or about 5-10 strokes per second.

The heating system could be any suitable system known by the skilled person, such as resistance heating. One preferred system is based on a commercially available semiconductive PTC heater.

FIG. 8 discloses yet another embodiment of the invention, which is designed for combined sterilisation as described above and ablation of the uterine endometrium, typically for treatment of menorrhagia. In this embodiment, the inflation lumen 4a extends in a tube 317 some distance into the balloon, beyond the branching point of the sterilisation lumen 4b. A pin 308, is arranged centrally in the tube 317. Around the pin 308 is wound a heater wire 318 which is in contact with the inflation fluid in the inflation lumen and adapted to heat the inflation fluid to a temperature of about 65-180° C., and preferably 75-90° C. if a water-based liquid is used as the inflation fluid. The heater is powered by means of electrical wires (not shown). The tube 317 is provided with a plurality of openings 310 for injection of the inflation fluid into the balloon. Optionally, the sterilisation apparatus may be adapted to circulate the inflation fluid within the balloon in order to achieve faster heating in the balloon. In such embodiments, the connector may comprise a fourth membrane similar to the first membrane described above, arranged to be in contact with the inflation fluid of the inflation lumen and operatively connected to driving means, such as a cam or a linear motor, for achieving a back and forth movement of the fourth membrane such that a circulation of inflation fluid may be obtained. By circulating the fluid in the inflation lumen after inflating the balloon, the inflation fluid in the balloon is circulated and continuously heated by the heater wire 318.

FIG. 8b discloses the cross section C-C from FIG. 8. It shows the relative position of the two sterilisation lumens 4b', which are located in parallel which each other. Furthermore, also the relative position of the two sterilisation lumens 4b' in relation to the enclosing inflation lumen 4a is illustrated, although said inflation lumen 4a is not enclosing the sterilisation lumens 4b' at the cross section C-C, but at a proximal position thereof.

Ablation of the uterine endometrium as described above may be performed before, after and/or during the sterilisation method described herein.

DETAILED DESCRIPTION Of ANOTHER PREFERRED EMBODIMENT OF THE INVENTION

Figure 9:
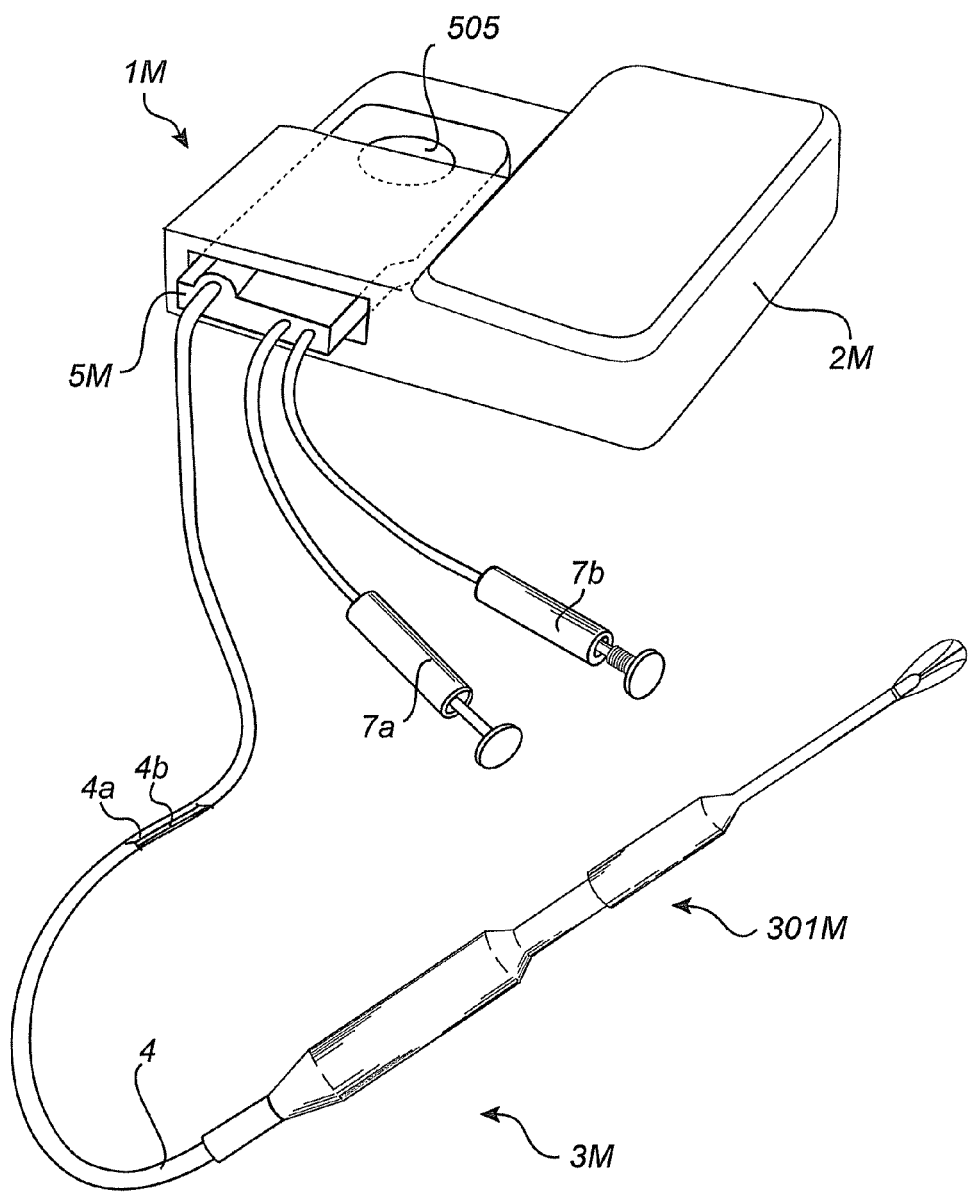
FIG. 9 shows a sterilisation apparatus according to another embodiment of the present invention.

Reference is made to FIG. 9, showing a sterilisation apparatus 1M. In this figure, there are certain components with similar or same function as in FIG. 1a-h belonging to the embodiment described above. Such components therefore have the same reference numeral as in FIG. 1a-h. To the extent that there are similar or corresponding components, but with a different function or feature, such components are referred to using the same reference numeral as in FIG. 1a-h followed by the index "M".

The sterilisation apparatus 1M of the present embodiment comprises a sterilisation catheter 3M which comprises a balloon catheter 301M, a conduit 4, a connector 5M, a first fluid lumen 4a, and a second fluid lumen 4b. The lumens 4a and 4b are contained in the conduit 4. The lumen 4a is connectable to a first injection syringe (inflation syringe) 7a and the lumen 4b is connectable to a second injection syringe (sterilisation syringe) 7b.

The first and the second fluid lumens 4a, 4b pass through the connector 5M which is partly inserted in a regulation unit 2M and provides connection between the sterilisation catheter 3M and the regulation unit 2M and the syringes 7a, 7b respectively.

The regulation unit 2M comprises means for inducing circulation of a sterilisation fluid within the second fluid lumen 4b and also comprises means for measuring the fluid pressure in the fluid lumen 4a. Furthermore the regulation unit 2M comprises heating means which provides for heating of the sterilisation fluid within the connector 5M. The regulation unit 2M provides electrical energy and means for controlling and regulating the temperature of said heater 20M. The regulation unit 2M also includes all necessary processors for operating and controlling the sterilisation apparatus 1M and for performing the method of the invention using said apparatus.

Between the regulation unit 2M and the connector 5M an interface is created which provides for transmission of heat and mechanical energy for the creation of circulation of the sterilisation fluid. The connector 5M is insertable and again removable from a suitably designed pocket in the regulation unit 2M by linear displacement.

The connector 5M is shown in detail in FIGS. 10a-c. The connector 5M is on its surface provided with means corresponding to the different means in the regulation unit 2M. The means in the regulation unit 2M for inducing circulation of the sterilisation fluid matches in the connector 5M a first membrane 501 and said means are adapted to create the back-and-forth movement of said membrane 501. The means in the regulation unit 2M for measuring the fluid pressure in the fluid lumen 4a comprises at least one fluid pressure sensor which is located in mechanical connection with a second membrane 502 in the connector 5M. The heating means in the regulation unit 2M comprises a heater 20M (shown in FIG. 10b, described in more detail below) which provides for heat to be transmitted to a fluid compartment 505 in the connector 5M connected to the second fluid lumen 4b and the membrane 501.

As in the embodiment described hereinbefore, the first lumen 4a (the inflation lumen) provides an inflation fluid path from the inflation syringe 7a through the connector 5M with the membrane 502 and enters the balloon catheter 301M via the conduit 4. In the present embodiment, the second lumen 4b, the sterilisation lumen, provides a sterilisation fluid path from the sterilisation syringe 7b via the membrane 501 and the fluid compartment 505 in the connector 5M and enters the balloon catheter 301M via the conduit 4.

FIG. 10a shows in more detail the connector 5M with the inflation fluid lumen 4a creating a fluid path via the membrane 502 to the conduit 4, and the sterilisation lumen 4b creating a fluid path over the membrane 501 and via the fluid compartment 505 to the conduit 4. FIG. 10b shows a cross-sectional view A-A of the connector 5M. The connector 5M comprises a compartment 505 having a circular and flat bottom portion and a at least partially cone-shaped top portion, a bottom 506 and a lid 507, creating a fluid tight space for containing sterilisation fluid, which space is connected with the lumen 4b during the sterilisation procedure. A sterilisation fluid lumen inlet 508 is provided in the wall of the fluid compartment 505 near the bottom 506 for inlet of sterilization fluid into the fluid compartment, and a sterilisation fluid lumen outlet 509 is provided in the top of the cone-shaped top portion for outlet of sterilisation fluid from the fluid compartment 505. "Inlet" and "outlet" are used for describing the intended flow of fluid when fluid is injected from the syringe 7b towards the sterilisation catheter. When the sterilisation fluid is circulated during operation of the apparatus, i.e. pumped back and forth in the sterilisation lumen, passing the fluid compartment 505, the inlet 508 functions alternatingly as an inlet and an outlet, as does the outlet 509.

The bottom 506 of the fluid compartment 505 is in thermal contact with the heater 20M provided in the regulation unit 2M. Preferably the part of the connector 5M containing the fluid compartment 505 is made at least partially of transparent material in order to allow visual control of the fluid flow during operation of the apparatus. The bottom 506 is one embodiment of a heat receiving portion according to the claims. The heater 20M is one embodiment of a heat emitting portion according to the claims.

The incorporation of the heater 20M in the regulation unit 2M, the heater 20M being in thermal contact with, but mechanically and electrically separated from the fluid compartment 505 in the connector 5M, has many advantages. One out of several benefits of this embodiment is that the design of the balloon catheter 301M can be considerably simplified in the absence of a heating system within it, and thus can be better adapted for mass production at much lower cost. This is also important from an environmental point of view if the sterile catheter is to be disposed after use. Furthermore, there is no way to contaminate the sterile liquid by the regulation unit 2M. Also, the heater 20M in the non-disposable regulation unit 2M may be produced with improved quality and more efficient technology may be chosen since it is used again and again.

It should be understood that the wording "thermal contact" is intended to incorporate any manner of transmitting heat from the heat emitting portion in the regulation unit 2M to the heat receiving portion in the connector 5M. Such manners may i.a. be electrical resistance heating, induction heating or microwave energy heating, but any manner that is found cost efficient and manageable in terms of size may be utilised.

From FIG. 9 it can be seen that the conduit 4 leaves the connector 5M at a vertical level somewhat higher than the lumens from the inflation syringe 7a and the sterilisation syringe 7b. The vertical level is determined by the vertical height of the compartment 505 and the level of the sterilisation fluid lumen outlet 509. Hereby any air which is drawn into the sterilisation fluid during treatment originating from the fallopian tubes 15 of the patient, or possibly during filling from the sterilisation syringe 7b, is pushed in front of the sterilisation fluid into the fallopian tube 15 at a subsequent forward stroke of the membrane 501. If the air would not be collected before again entering the fallopian tubes 15 there would be a risk for the creation of an air pillar encapsulated in the sterilisation fluid in the sterilisation lumen 4b. Such an air pillar would hinder the sterilisation fluid on the distal side of the air pillar to enter the compartment 505 and hence from proper heating. Thus an improper treatment could take place. The compartment 505 may be seen as an air-fluid separator. The treatment sequence will be further discussed in connection with FIGS. 12a-d.

FIG. 10c shows a side view of the connector of FIG. 10a.

Figure 11:
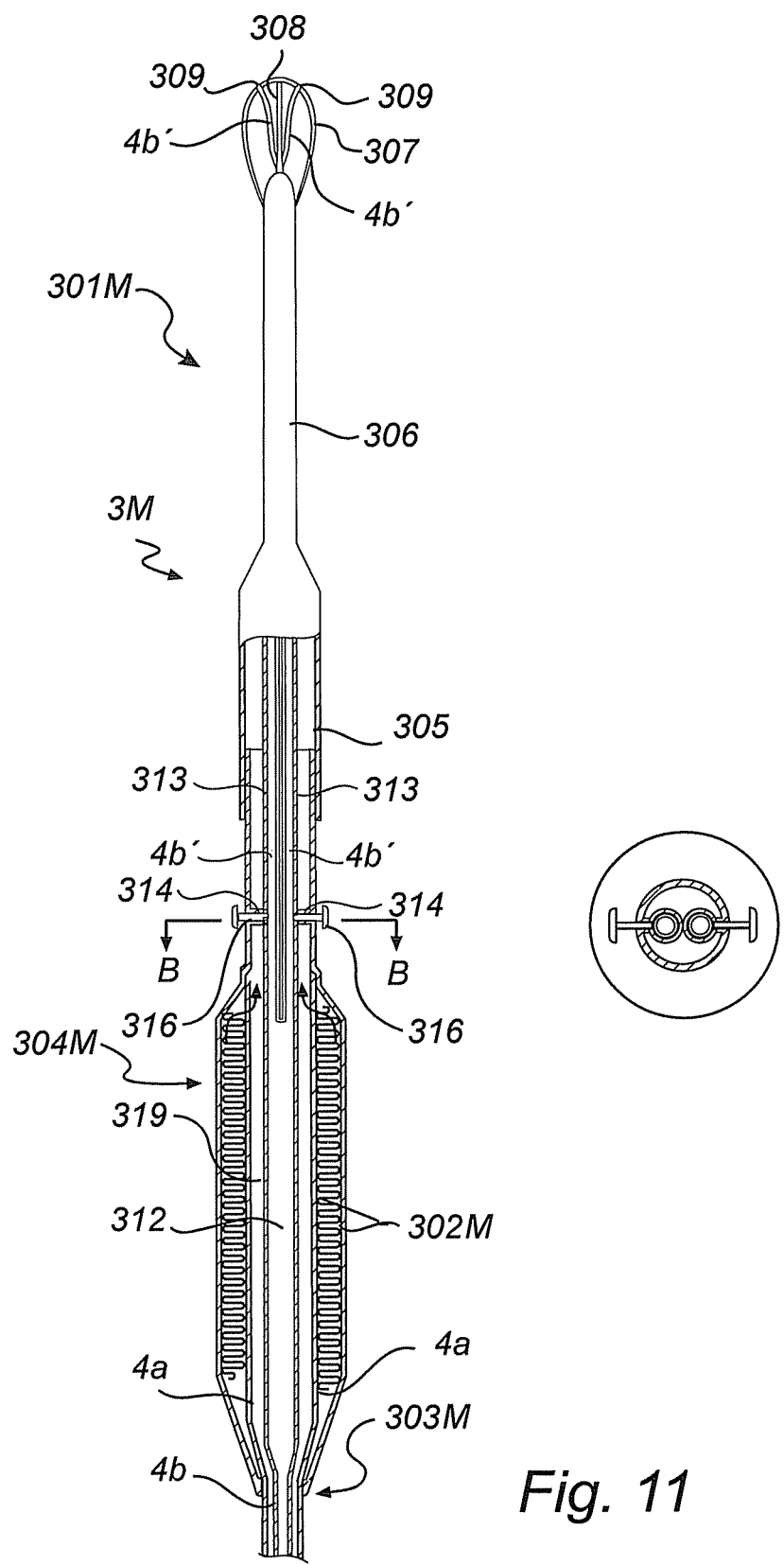

FIG. 11 illustrates the simplified balloon catheter 301M partly in cross-section. The balloon catheter 301M comprises an elongated tubular body 304M. In the proximal part is a handle 302M provided for the operator of the sterilisation apparatus 1M. The middle and distal part of the balloon catheter comprises a tube containing at least one lumen (corresponding to FIG. 1f). The outmost, distal part of the balloon catheter 301M comprises an elongation of said tube in the form of a pin 308 which is fixed to a balloon 307 at the inside wall of a distal part of the balloon 307.

The distal part 306 of the shaft 305 is narrow to allow easy introduction into the uterus via the cervix and has a length bridging at least the length of the vagina and the cervix. The collar of the balloon 307 is outwardly fixed to the distal part of the shaft 305 in a fluid tight manner.

The inflation lumen 4a and the centrally located sterilisation lumen 4b exit the conduit 4 and enter the hollow balloon catheter 301M at the proximal end 303M of the handle 302M. The fluid lumens 4a and 4b subsequently pass through the tubular body 304M and the shaft 306 and arrive at the distal part of the balloon catheter 301M. One inflation lumen 4a is provided for inflation of the balloon 307. Having entered the handle 302M, the inflation lumen 4a passes outside the central sterilisation lumen 4b and through the shaft 306 to the distal part of the balloon catheter 301M, where the inflation lumen 4a debouches into the balloon 307 via one or more openings (corresponds to FIG. 1f). The inflation lumen 4a forms part of a closed, pressurized inflation system intended for inflation of the balloon 307 by means of a fluid, e.g. a gas, such as air, or a liquid, such as water or saline.

Furthermore, as illustrated in FIG. 11, a sterilisation fluid lumen 4b is provided for injection and circulation of sterilisation fluid. The sterilisation lumen 4b enters the handle 302M at the proximal end 303M, and branches into two initially parallel, preferably flexible, sterilisation lumens 4b', each one arranged in a rigid tube 313 which continues through the distal part of the balloon catheter 301M into the balloon 307.

Close to the handle 302M, opposing channels 314 ending in openings are provided in the wall of the tubular body 304M. Corresponding openings (not shown) are provided in the respective walls of the tubes 313, which enable alternately blocking the provision of fluid to each sterilisation lumen 4b' by means of a clamping device 316 so that fluid may pass through only one sterilisation lumen 4b' at a time. Thus, treatment of only one fallopian tube 15 at a time may be performed.

The two sterilisation lumens 4b' leave the tubes 313 in the balloon in the form of two flexible tubes of fine calibre. The sterilisation lumens 4b' debouch at the outer face of the balloon 307 via debouching openings 309 as shown in FIG. 11. The sterilisation lumens thus create fluid paths from the sterilisation syringe 7b to the atmosphere surrounding the balloon 307. The fluid within the sterilisation lumen 4b is never in contact with the inner atmosphere of the balloon 307, which may comprise an inflation fluid inside the balloon 307. The sterilisation lumens 4b' are attached to the balloon 307 at their respective debouching openings 309. The sterilisation lumen(s) form(s) part of an open injection system for injection, circulation and optionally retraction of sterilisation fluid in the fallopian tubes 15.

Hence, the sterilisation fluid circulation system, which also comprises sterilisation syringe 7b, is separate from the closed inflation system, and there is no fluid communication between these systems.

It should be noted that the conduit 4 extending between the connector 505 and the balloon catheter 301M does not contain any heater and corresponding electrical wires or other supply lumens as in the earlier disclosed preferred embodiments of the invention as shown in FIGS. 1a-i and denoted 4c, thereby simplifying the design of the catheter.

Figures 12A, 12B:
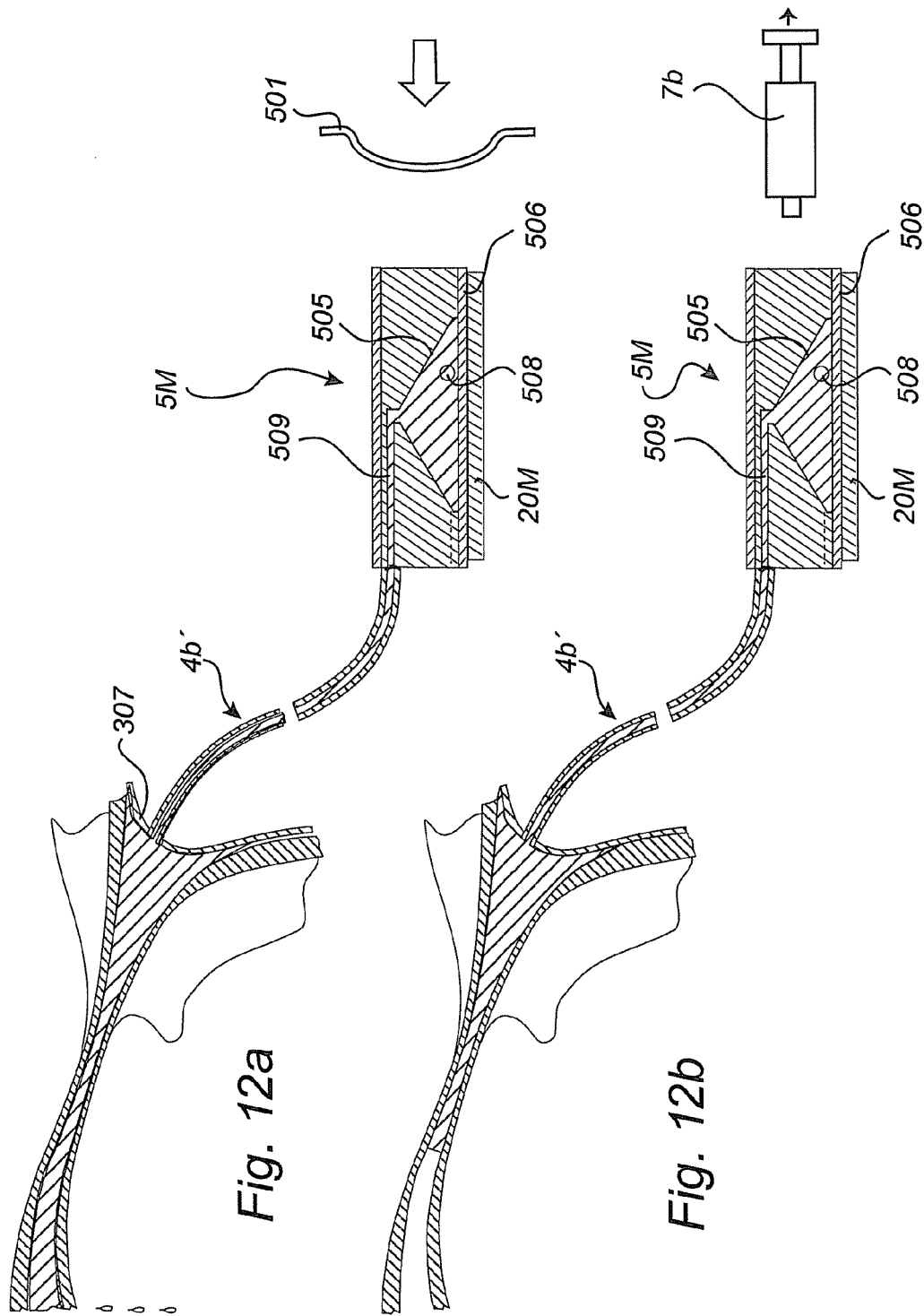

The preparations for performing the sterilisation method using the apparatus according to the present embodiment will now be described in connection with FIGS. 9, 10a and 12a. Before insertion of the sterilisation apparatus into the uterine cavity of the patient, the sterilisation lumen 4b may be at least partly filled with sterilisation fluid. This is performed with the regulation unit 2M kept in horizontal position and the connector 5M connected to the regulation unit 2M. In this position the bottom 506 of the connector 5M is in close contact with the heater 20M allowing good heat transmission from the heater 20M to the fluid compartment 505. The syringe 7b is filled with sterilisation fluid and connected to the sterilisation lumen 4b, the valve 8b is opened and a desired volume of fluid is injected into the sterilisation lumen 4b filling the pulse mediator membrane 501 and the compartment 505. The balloon catheter 301M is inserted into the uterine cavity 17 with the balloon 307 uninflated. When the balloon catheter 301M has been positioned, filled and pressurised with inflation fluid via inflation syringe 7a according to the earlier described embodiment, sterilisation fluid is brought into the fallopian tube or tubes 15 to be treated. Such an amount of sterilisation fluid is used that the fallopian tube(s) 15 is completely filled and such that some small volume of sterilisation fluid is running out at the other end. This is illustrated in FIG. 12a by droplets at the far left. This is possible since the sterilisation fluid preferably is sterile water and at a temperature which is not harmful for the patient at this stage.

As a next step the syringe 7b is retracted by the user a known amount, corresponding to a predefined certain volume. This volume is small and may be decided upon in each specific case. The syringe 7b is provided with a screw in order to be able to fine tune this volume. This position corresponds to a first end point of the sterilisation treatment. This situation is shown in FIG. 12b.

In the following step, according to FIG. 12c, the means for inducing circulation of the sterilisation fluid in the regulation unit 2M is retracting the membrane 501 and thus the sterilisation fluid to a position in which air is entering and clearly visible at the top portion of the transparent compartment 505. When air is entering the compartment 505 the user of the sterilisation apparatus knows that the fallopian tube(s) 15 is essentially empty. This position corresponds to a second end point of the sterilisation treatment. Furthermore, the volume to be treated is now well defined since the user can calculate the volume of the system based upon the two end positions after the small retraction in FIG. 12b and the essentially complete retraction of FIG. 12c and information on the specific and well defined volume of the sterilisation apparatus.

Now the actual sterilisation is initiated. In FIG. 12d the membrane 501 thus drives the sterilisation fluid into the fallopian tube(s) 15 up to the level which was decided upon according to FIG. 12b. The heater 20M, which is located in direct contact with the bottom 506 of the compartment 505, is also beginning to heat the sterilisation fluid. Then, as is seen in FIG. 12e, the membrane 501 draws the sterilisation fluid back into the compartment 505 to the level seen in FIG. 12c were it is reheated. The pulsation or circulation (i.e. the driving of the sterilisation fluid between the situations in FIGS. 12d and 12e) of the sterilisation is performed according what is described in connection with the earlier embodiments of the invention and is performed first until the sterilisation fluid is reaching its desired temperature, and then until a time period needed for a full sterilisation to take place is reached, during which the temperature is kept at this level. FIG. 7 is exemplifying such a cycle.

In order to accomplish the desired manoeuvrability of the membrane 501a stepper motor and a linear motor is used which are located in the regulation unit 2M. The linear motor is driving the back-and-forth movement of the membrane 501 in a volumetric movement. The stepper motor is ensuring that each time the apparatus is paused or stopped the membrane 501 is stopped in a retracted position such that a continuation of the treatment would cause a backward stroke.

One major advantage with a transparent compartment 505 having a top portion which is narrower than the bottom 506 in combination with withdrawal of the sterilisation fluid until air is seen is that the user of the sterilisation apparatus can be confident that sterilisation treatment is taking place. It may be during installation that the sterilisation lumen 4b' is positioned slightly wrong or offset in relation to the tubal ostium and the fallopian tube 15 such that the sterilisation fluid does not enter the fallopian tube 15. Another obstacle that might occur is the occurrence of cramps in the fallopian tube 15 leading to temporary occlusion thereof. When filling the sterilisation apparatus and the selected portions of the patient under these conditions, the sterilisation fluid still must exit somewhere. The circulation of sterilisation fluid is a hydrostatic volumetric pumping and is consequently still continuing although the presence of obstacles.

In FIGS. 13a and 13b a situation with an occluded fallopian tube 15 is illustrated. In FIG. 13a the sterilisation fluid is drawn into the compartment 505. Yet no air is drawn into the compartment 505. When sterilisation fluid is driven into the occluded fallopian tube 15 the balloon 307 will bend and give way for the circulated volume of sterilisation fluid. Thus, when retracting the sterilisation fluid into the compartment 505, there is no air since the sterilisation fluid has not come in contact with any. As a consequence no air will become visible and the user can determine that the sterilisation apparatus probably should be repositioned or that a correct treatment is not taking place. Consequently, the presence of air, which comes and goes during treatment, i.e. when changing between the situations of FIGS. 13a and 13b, is visual proof of a correct treatment of the patient.

Many further alternative embodiments of the present invention may be contemplated within the scope of the claims. For example, the balloon 307 may be replaced by two separate, smaller balloons positioned further along the sterilisation lumens 4b' such as to, when inflated, fill the uterine cornu, thereby separating the tubal ostium from the uterine cavity. In another alternative embodiment the balloon catheter may comprise only one sterilisation lumen 4b', such that only one fallopian tube 15 may be treated. In yet another alternative, each sterilisation lumen 4b' may comprise two individual lumens, one lumen for injecting sterilisation fluid and one lumen for retracting sterilisation fluid. In a further embodiment the compartment 505 in the connector 5M may be designed differently, such as having a square bottom 506 and other height shape. Also, in the embodiment of the invention having separable heat receiving portions and heat emitting portions the compartment 505 comprises a membrane 501 connected to a linear motor which may be regulated by the user in terms of length of stroke. The reason being that the uterus and accompanying organs of different patients quite often vary in size and volume. Hence there is a wish to design an apparatus which is adequately adjustable to the different patients. However, instead it may be useful to simplify the design of the apparatus and design one which encompasses a larger volume of sterilisation fluid such that both small and large volume patients may be treated. Hence the compartment 505 may be made larger and the length of stroke be set constant. In order to treat a small volume patient, the volume of sterilisation fluid inserted into the apparatus is thus made adequately small resulting in a situation in which more air is entering into the compartment 505 and thus a larger circle of air is visible for the user.

Furthermore, any embodiment of the invention as disclosed herein may be combined in parts or in full with any of the other embodiments disclosed herein.

The invention claimed is:

1. An apparatus for sterilisation of a female mammal comprising:
   at least one separation member for separation of a fallopian tube from a uterine cavity of the female mammal, the at least one separation member including an inflatable member,
   a circulation assembly which is operatively connected to said at least one separation member, and
   at least one sterilisation lumen which is operatively connected to said circulation assembly and debouching at a distal side of said at least one separation member, said at least one sterilisation lumen being adapted for injection in use of a tissue necrotising fluid through at least one debouching opening, the at least one debouching opening extending from an inner surface to an outer surface of a wall of the inflatable member, the tissue necrotising fluid capable of necrotising a lining of at least a part of said fallopian tube, the at least one sterilisation lumen terminating at the at least one debouching opening,
   wherein said circulation assembly is adapted to circulate said tissue necrotising fluid within said sterilisation lumen and said fallopian tube, and
   wherein the at least one sterilisation lumen is configured to isolate the tissue necrotising fluid from the inner surface of the wall of the inflatable member during the injection.

2. The apparatus according to claim 1, wherein said circulation assembly is adapted to drive a set volume of said tissue necrotising fluid back and forth into said fallopian tube during a treatment period.

3. The apparatus according to claim 2, wherein said back and forth movement is driven at a generally constant frequency.

4. The apparatus according to claim 2, wherein said circulation assembly comprises moving means connected to said sterilisation lumen and a driving mechanism, which driving mechanism in use is adapted to move said moving means back and forth, thereby oscillating said tissue necrotising fluid between said sterilisation lumen and a location within said fallopian tube.

5. The apparatus according to claim 4, wherein said circulation assembly, when stopped after a treatment period is finished, is adapted to cause said moving means to start a back movement when a new treatment period is initiated.

6. The apparatus according to claim 4, wherein said driving mechanism is a stepper motor.

7. The apparatus according to claim 4, wherein said moving means is a flexing membrane which is positioned in line with the tissue necrotising fluid.

8. The apparatus according to claim 1, wherein said at least one separation member is adapted to separate the tubal ostium of a fallopian tube from the uterine cavity of the female mammal.

9. The apparatus according to claim 1, wherein a distal end of said at least one sterilisation lumen comprises the at least one debouching opening and, in use, is positioned in or in the proximity of said fallopian tube.

10. The apparatus according to claim 9, wherein said at least one separation member is adapted to simultaneously separate both fallopian tubes from the uterine cavity.

11. The apparatus according to claim 10, wherein said at least one sterilisation lumen includes two sterilisation lumens, each debouching in or in the proximity of a separate fallopian tube.

12. The apparatus according to claim 11, wherein said circulation assembly and said sterilisation lumens are adapted for treatment of both fallopian tubes simultaneously.

13. The apparatus according to claim 11, further comprising:
a clamping device operatively connected to said sterilisation lumens and arranged to separately clamp one of said two sterilisation lumens so as to prevent passage of fluid through said one sterilisation lumen.

14. The apparatus according to claim 13, further comprising:
a pressure sensor arranged to detect a fluid pressure in one of said two sterilisation lumens.

15. The apparatus according to claim 1, further comprising:
an inflation assembly adapted to inflate said inflatable member by introducing an inflation fluid via at least one inflation lumen.

16. The apparatus according to claim 1, wherein said at least one sterilisation lumen is positioned within said inflatable member.

17. The apparatus according to claim 1, wherein said circulation assembly is adapted to heat said tissue necrotising fluid to a temperature of about 65-180° C.

18. The apparatus according to claim 17, wherein said circulation assembly includes a heater provided on a proximal side of said at least one separation member adapted to heat said tissue necrotising fluid.

19. The apparatus according to claim 1, wherein said at least one separation member includes an ablation member for ablation of uterine tissue in the female mammal.

20. The apparatus according to claim 19, wherein said ablation member is the inflatable member.

21. The apparatus according to claim 1, further comprising:
heating means provided on a proximal side of said at least one separation member for heating said tissue necrotising fluid, said heating means having a heat emitting portion and a heat receiving portion which in use of the apparatus are positioned in thermal contact with each other, and which are separable from each other.

22. The apparatus according to claim 21, wherein said apparatus is separable into a reusable unit and a disposable unit, said disposable unit being adapted to be sterile.

23. The apparatus according to claim 22, wherein said heat emitting portion is positioned in said reusable unit and said heat receiving portion is positioned in said disposable unit.

24. The apparatus according to claim 22, wherein said reusable unit comprises a regulation unit.

25. The apparatus according to claim 22, wherein said circulation assembly comprises a fluid compartment in fluid connection with said sterilisation lumen, a wall of said fluid compartment at least partly forming said heat receiving portion.

26. The apparatus according to claim 25, wherein said fluid compartment is connected to a proximal part of the sterilisation lumen via a fluid inlet opening and is connected to a distal part of the sterilisation lumen via a fluid outlet opening.

27. The apparatus according to claim 26, wherein said fluid compartment has an at least partly conical shape, comprising a wider bottom portion and a narrower top portion as seen in a vertical direction.

28. The apparatus according to claim 27, wherein said fluid inlet opening is located near the bottom portion of the fluid compartment and the outlet opening is located at the top portion of the fluid compartment.

29. The apparatus according to claim 21, wherein said heating means are heated by any of the methods chosen from the group of electric resistance heating, induction heating, microwave energy heating, and semi-conductive ceramic elements.

30. The apparatus according to claim 21, wherein said heat emitting portion is a tempered surface and is in use of the apparatus positioned in mechanical contact with the heat receiving portion.

31. The apparatus according to claim 1, wherein said circulation assembly is adapted to heat said tissue necrotising fluid to a temperature of about 75-90° C.

32. The apparatus according to claim 1, wherein said at least one separation member is configured to isolate the fallopian tube from the uterine cavity of the female mammal.

33. The apparatus according to claim 1, wherein an inner surface of the at least one sterilisation lumen is distinct from the inner surface of the wall of the inflatable member.

34. A method for sterilisation of a female mammal, comprising steps of:
(a) separating the tubal ostium of a fallopian tube from the uterine cavity of the female mammal, the separating including an inflation of an inflatable member by introduction of an inflation fluid into the inflatable member;
(b) after the separating, injecting a tissue necrotising fluid via an sterilisation lumen at a position which is in communication with said fallopian tube, the injecting being performed through a debouching opening, the debouching opening extending from an inner surface to an outer surface of a wall of the inflatable member, the sterilisation lumen terminating at the debouching opening; and
(c) after the injecting, circulating said tissue necrotising fluid within said sterilisation lumen and said fallopian tube,
wherein the sterilisation lumen is configured to isolate the tissue necrotising fluid from the inner surface of the wall of the inflatable member during the injection.

35. The method according to claim 34, wherein the step of circulating said tissue necrotising fluid comprises oscillating a set volume of said tissue necrotising fluid back and forth into said fallopian tube.

36. The method according to claim 35, wherein the step of oscillating is accomplished by a driving mechanism connected to moving means such that said tissue necrotising fluid is moving back and forth between said sterilisation lumen and a location within said fallopian tube.

37. The method according to claim 35, wherein said volume of tissue necrotising fluid is set prior to initiation of a treatment period by
(b1) injecting said tissue necrotising fluid in to said fallopian tube until it is essentially filled, and
(b2) retracting a predefined volume of said tissue necrotising fluid.

38. The method according to claim 34, wherein both fallopian tubes of a female mammal are simultaneously separated from said uterine cavity.

39. The method according to claim 38, wherein steps (b) and (c) are performed on each fallopian tube separately.

40. The method according to claim 34, wherein said tissue necrotising fluid during circulation thereof into the fallopian tube is heated to a temperature of 65-180° C.

41. The method according to claim 34, wherein said tissue necrotising fluid comprises a fluid selected from the group consisting of sterile water, saline, glycerine, glucose, mannitol, glycerine based liquids, and combinations thereof.

42. The method according to claim 34, comprising, before step (c), a step of (b1) injecting a fluid into the fallopian tube via said sterilisation lumen and monitoring a fluid pressure within the sterilisation lumen for determining whether the fallopian tube is open or closed.

43. The method according to claim 34, further comprising: ablating uterine tissue in the female mammal.

44. The method according to claim 43, wherein said step of ablating uterine tissue is performed using said inflatable member.

45. The method according to claim 34, wherein the method is performed with an apparatus including at least one separation member for separation of said fallopian tube from said uterine cavity of the female mammal, a circulation assembly which is operatively connected to said at least one separation member, and said sterilisation lumen which is operatively connected to said circulation assembly and debouching at a distal side of said at least one separation member, said at least one sterilisation lumen being adapted for injection in use of said tissue necrotising fluid capable of necrotising a lining of at least a part of said fallopian tube, wherein said circulation assembly is adapted to circulate said tissue necrotising fluid within said sterilisation lumen and said fallopian tube.

46. The method according to claim 34, wherein said tissue necrotising fluid during circulation thereof into the fallopian tube is heated to a temperature of 75-90° C.

* * * * *